United States Patent [19]

Whittaker et al.

[11] Patent Number: 5,446,032
[45] Date of Patent: Aug. 29, 1995

[54] IMIDAZO (4,5-C) PYRIDINE DERIVATIVES AS PAF ANTAGONISTS

[75] Inventors: Mark Whittaker; Andrew Miller, both of Oxford, England

[73] Assignee: British Biotech Pharmaceuticals Limited, Oxford, United Kingdom

[21] Appl. No.: 185,815

[22] PCT Filed: Jul. 24, 1992

[86] PCT No.: PCT/GB92/01370

§ 371 Date: Feb. 28, 1994

§ 102(e) Date: Feb. 28, 1994

[87] PCT Pub. No.: WO93/02080

PCT Pub. Date: Feb. 4, 1993

[30] Foreign Application Priority Data

Jul. 24, 1991 [GB] United Kingdom ............ 9116056

[51] Int. Cl.⁶ .............. A61K 31/435; C07D 471/04
[52] U.S. Cl. ................. 514/63; 514/303; 546/14; 546/118
[58] Field of Search ............. 546/118, 14; 514/303, 514/63

[56] References Cited

U.S. PATENT DOCUMENTS 4,914,108  4/1990  Khanna et al. ............ 514/303

FOREIGN PATENT DOCUMENTS

| 0144804A | 6/1985 | European Pat. Off. |
| 0238202A | 9/1987 | European Pat. Off. |
| 260613A | 6/1988 | European Pat. Off. |
| 0344414 | 12/1989 | European Pat. Off. |
| 8908653A | 9/1989 | WIPO |
| 90/09997 | 9/1990 | WIPO |
| WO92/03423 | 3/1992 | WIPO |

*Primary Examiner*—Bernard Dentz
*Attorney, Agent, or Firm*—Banner & Allegretti, Ltd.

[57] ABSTRACT

Compounds of formula I:

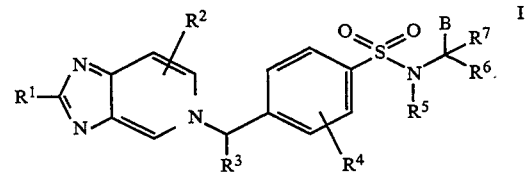

wherein $R^1$, $R^2$, $R^3$, $R^4$, $R^5$, $R^6$, $R^7$, $R^8$, $R^9$, and B are variables. These compounds are antagonists of platelet activating factor (PAF) and as such are useful in the treatment or amelioration of various diseases or disorders mediated by PAF.

16 Claims, No Drawings

IMIDAZO (4,5-C) PYRIDINE DERIVATIVES AS PAF ANTAGONISTS

This application is a 371 of PCT/GB92/01370 filed Jul. 24, 1992.

This invention relates primarily to novel compounds which are antagonists of platelet activating factor.

Platelet activating factor (PAF) is a bioactive phospholipid which has been identified as 1-O-hexadecyl-/octadecyl-2-acetyl-sn-glyceryl-3-phosphoryl choline. PAF is released directly from cell membranes and mediates a range of potent and specific effects on target cells resulting in a variety of physiological responses which include hypotension, thrombocytopenia, bronchoconstriction, circulatory shock, and increased vascular permeability (oedema/erythema). It is known that these physiological effects occur in many inflammatory and allergic diseases and PAF has been found to be involved in a number of such disorders including asthma, endotoxin shock, adult respiratory distress syndrome, glomerulonephritis, immune regulation, transplant rejection, gastric ulceration, psofiasis, and cerebral myocardial and renal ischemia. Thus the compounds of the invention, by virtue of their ability to antagonise the actions of PAF, should be of value in the treatment of any of the above disorders and any other conditions in which PAF is implicated (e.g. embryo implantation).

Compounds which have been disclosed as possessing activity as PAF antagonists include compounds which are strutrurally related to the PAF molecule such as glycerol derivatives (EP-A-0238202), and heterocyclic compounds such as 2,5-diaryl tetrahydrofurans (EP-A-0144804) and imidazopyridine derivatives (EP-A-0260613 and WO-A-8908653).

U.S. Pat. No. 4,914,108 discloses a series of imidazo[4,5-c]pyridines substituted at the pyridine ring nitrogen atom (5-position) with a side chain consisting of an alkyl group linked to a phenylene ring. However, the compounds disclosed therein terminate in a carboxamide group, —C(O)NRR In marked contrast, the present invention provides novel and useful sulphonamide derivatives of α-amino acids and of α-amino alcohols and their pharmaceutically acceptable acid addition salts. and pharmaceutical uses thereof as PAF antagonists.

According to a first aspect of the invention there is provided a compound of general formula I;

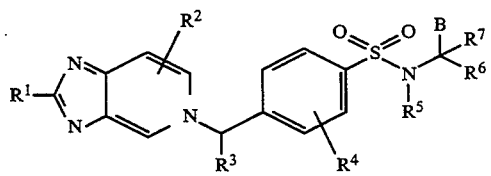

wherein:
each of $R^1$ and $R^3$ independently represents hydrogen or a —$C_1$-$C_6$ alkyl group;
$R^2$ represents a group substituted at one or more of the 4, 6 or 7 positions of the imidazo[4,5-c]pyridine heterocycle, said group(s) being independently selected from hydrogen, —$C_1$-$C_6$ alkyl, —$OC_1$-$C_6$ alkyl, or halogen;
$R^4$ represents hydrogen, —$C_1$-$C_6$ alkyl, —$OC_1$-$C_6$ alkyl, or a halogen;
$R^5$ represents hydrogen, —$C_1$-$C_6$ alkyl, —$C_2$-$C_6$ alkenyl, —$C_2$-$C_6$ alkynyl, —$COC_1$-$C_6$ alkyl, —$CO_2C_1$-$C_6$ alkyl, —($COC_1$-$C_6$ alkyl)phenyl, —(-$CO_2C_1$-$C_6$ alkyl)phenyl, —($C_1$-$C_6$ alkyl)$OC_1$-$C_6$ alkyl, —($C_1$-$C_6$ alkyl)$SC_1$-$C_6$ alkyl, —($C_1$-$C_6$ alkyl)$CO_2C_1$-$C_6$ alkyl, —$C_3$-$C_8$ cycloalkyl, —$C_4$-$C_8$ cycloalkenyl or a group —D wherein D represents a group;

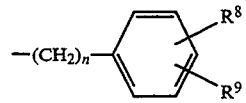

wherein n is an integer from 0 to 3, and each of $R^8$ and $R^9$ is independently hydrogen, —$C_1$-$C_6$ alkyl, —$C_2$-$C_6$ alkenyl, —$C_2$-$C_6$ alkynyl, halogen, —CN, —$CO_2H$, —$CO_2C_1$-$C_6$ alkyl, —$CONH_2$, —$CONHC_1$-$C_6$ alkyl, —$CON(C_1$-$C_6$ alkyl)$_2$, —CHO, —$CH_2OH$, —$CF_3$, —$OC_1$-$C_6$ alkyl, —$SC_1$-$C_6$ alkyl, —$SOC_1$-$C_6$ alkyl, —$SO_2C_1$-$C_6$ alkyl, —$NH_2$ or -NHCOMe:
each of $R^6$ and $R^7$ independently represent hydrogen, halogen, —$C_1$-$C_6$ alkyl optionally substituted by one or more halogen atoms, —$C_2$-$C_6$ alkenyl, —$C_2$-$C_6$ alkynyl, —($C_1$-$C_6$ alkyl)$CO_2C_1$-$C_6$ alkyl, —($C_1$-$C_6$ alkyl)$SC_1$-$C_6$ alkyl, —($C_1$-$C_6$ alkyl)$OC_1$-$C_6$ alkyl, —($C_1$-$C_6$ alkyl)$N(C_1$-$C_6$ alkyl)$_2$, $C_3$-$C_8$ cycloalkyl, —$C_4$-$C_8$ cycloalkenyl, —($C_1$-$C_6$ alkyl)$C_3$-$C_8$ cycloalkyl, —($C_1$-$C_6$ alkyl)$C_4$-$C_8$ cycloalkenyl, —($C_1$-$C_6$ alkyl) $OC_3$-$C_8$ cycloalkyl, —($C_1$-$C_6$ alkyl) $OC_4$-$C_8$ cycloalkenyl, —($C_1$-$C_6$ alkyl)$SC_3$-$C_8$ cycloalkyl, —($C_1$-$C_6$ alkyl)$SC_4$-$C_8$ cycloalkenyl, a side chain of a naturally occurring amino acid, a group —D, or a —($C_1$-$C_6$ alkyl)OD group wherein D is as defined above:
or $R^5$ together with $R^6$ or $R^7$ and the atoms to which they are attached form a 5 to 8 membered nitrogen-containing heterocyclic ring;
or $R^6$ and $R^7$ together with the carbon atom to which they are attached form a $C_3$-$C_8$ cycloalkyl ring;
B represents a) a —$(CH_2)_mA$ group wherein m is an integer from 0 to 1 and the group A represents a 5- or 6-membered heterocyclic ring, which heterocyclic ring may be optionally fused to a benzene ring or to a further 5-, 6- or 7-membered heterocyclic ring containing one or more nitrogen atoms, wherein at least one of the said heterocyclic rings may also contain an oxygen or sulphur atom, and wherein any of the rings may be optionally substituted with one or more substituents selected from hydrogen, halogen, —$C_1$-$C_4$ perfloroalkyl, hydroxyl, carbonyl, thiocarbonyl, carboxyl, —$CONH_2$, a group —D wherein D is as defined above, —$R^{10}$, —$OR^{10}$, —$SR^{10}$, —$SOR^{10}$, —$SO_2R^{10}$, —$NHR^{10}$, —$NR^{10}R^{10}$, —$CO_2R^{10}$ or —$CONHR^{10}$ wherein $R^{10}$ is —$C_1$-$C_6$ alkyl, —$C_2$-$C_6$ alkenyl, —$C_2$-$C_6$ alkynyl, —$C_3$-$C_8$ cycloalkyl or —$C_4$-$C_8$ cycloalkenyl each of which is optionally substituted with one or more substituents selected from halogen, hydroxyl, amino, carboxyl, —$C_1$-$C_4$ perfluoroalkyl, —$C_1$-$C_6$ alkyl, —$C_2$-$C_6$ alkenyl, —$C_2$-$C_6$ alkynyl, —$C_3$-$C_8$ cycloalkyl, —$C_4$-$C_8$ cycloalkenyl, —$OC_1$-$C_6$ alkyl, —$SC_1$-$C_6$ alkyl, tetrazol-5-yl, a group —D wherein D is as defined above or a heteroaryl or heteroarylmethyl group:
b) a —$ZR^{11}$ group wherein Z is —C(=O) —, —C(=O)O—, —C(=O)S —, —($C_1$-$C_6$ alkyl)O—, —($C_1$-$C_6$ alkyl)OC(=O) —, —C(=S) —, —C(=

S)O—, —($C_1$-$C_6$ alkyl)S —, —($C_1$-$C_6$ alkyl)OC(=O)C(=O)O—, —($C_1$-$C_6$ alkyl)OSO$_2$—, —NHC(=O)O—, —($C_1$-$C_6$ alkyl)OC(=O)NH —, —($C_1$-$C_6$ alkyl)C(=O)O— group, or —($C_1$-$C_6$ alkyl)OSi($C_1$-$C_6$ alkyl)$_2$—, —($C_1$-$C_6$ alkyl)OSiPh$_2$— group and $R^{11}$ is hydrogen, —$C_1$-$C_{18}$ alkyl, —$C_2$-$C_{18}$ alkenyl, —$C_2$-$C_{18}$ alkynyl, —($C_1$-$C_6$ alkyl)O$C_1$-$C_6$ alkyl, —($C_1$-$C_6$ alkyl)S$C_1$-$C_6$ alkyl, —($C_1$-$C_6$ alkyl)O($C_1$-$C_6$ alkyl)O$C_1$-$C_6$ alkyl, —$C_3$-$C_8$ cycloalkyl, —$C_4$-$C_8$ cycloalkenyl, a group D as defined above or a group A as defined above:

c) a —CH$_2$NR$^{12}$R$^{13}$ group or a —CONR$^{12}$R$^{13}$ group wherein each of $R^{12}$ and $R^{13}$ is independently hydrogen, —$C_1$-$C_6$ alkyl, —$C_3$-$C_8$ cycloalkyl, pyridyl, a group D as defined above or $R^{12}$ and $R^{13}$ together with the nitrogen atom to which they are attached form a 5 to 8 membered nitrogen-containing heterocyclic ring;

or a pharmaceutically or veterinarily acceptable acid addition salt or hydrate thereof.

Hereafter in this specification the term "compound" includes "salt" or "hydrate" unless the context requires otherwise.

As used herein the term "halogen" or its abbreviation "halo" means fluoro. chloro, bromo or iodo.

As used herein the term "$C_1$-$C_6$ alkyl" refers to straight chain or branched chain hydrocarbon groups having from one to six carbon atoms. Illustrative of such alkyl groups are methyl, ethyl, propyl, isopropyl, butyl, isobutyl, sec-butyl, t-butyl, pentyl, neopentyl and hexyl.

As used herein the term "$C_1$-$C_{18}$ alkyl" refers to straight chain or branched chain hydrocarbon groups having from one to eighteen carbon atoms. Illustrative of such alkyl groups are methyl, ethyl, propyl, isopropyl, butyl, isobutyl, sec-butyl, t-butyl, pentyl, neopentyl, hexyl, decyl, dodecyl, tridecyl, tetradecyl, pentadecyl, hexadecyl, heptadecyl, and octadecyl. From one to six carbon atoms may be preferred.

As used herein the term "$C_2$-$C_6$ alkenyl" refers to straight chain or branched chain hydrocarbon groups having from two to six carbon atoms and having in addition one double bond, of either E or Z stereochemistry where applicable. This term would include for example, vinyl, 1-propenyl, 1- and 2-butenyl and 2-methyl-2-propenyl.

As used herein the term "$C_2$-$C_{18}$ alkenyl" refers to straight chain or branched chain hydrocarbon groups having from two to eighteen carbon atoms and having in addition one or more double bonds of either E or Z stereochemistry where applicable. This term would include for example vinyl, 1-propenyl, 1- and 2-butenyl, 2-methyl-2-propenyl, geranyl, and farnesyl. From two to six carbon atoms may be preferred.

As used herein the term "$C_2$-$C_6$ alkynyl" refers to straight chain or branched chain hydrocarbon groups having from two to six carbon atoms and having in addition one triple bond. This term would include for example, ethynyl, 1-propynyl, 1- and 2-butynyl, 2-methyl-2-propynyl, 2-pentynyl, 3-pentynyl, 4-pentynyl, 2-hexynyl, 3-hexynyl, 4-hexynyl and 5-hexynyl.

As used herein the term "$C_2$-$C_{18}$ alkynyl" refers to straight chain or branched chain hydrocarbon groups having from two to six carbon atoms and having in addition one triple bond. This term would include for example, ethynyl, 1-propynyl, 1- and 2-butynyl, 2-methyl-2-propynyl, 2-pentynyl, 3-pentynyl, 4-pentynyl, 2-hexynyl, 3-hexynyl, 4-hexynyl, 5-hexynyl, 10-undecynyl, 4-ethyl-1-octyn-3-yl, 7-dodecynyl, 9-dodecynyl, 10-dodecynyl, 3-methyl-1-dodecyn-3-yl, 2-tridecynyl, 11-tridecynyl, 3-tetradecynyl, 7-hexadecynyl and 3-octadecynyl. From two to six carbon atoms may be preferred.

As used herein the term "$C_1$-$C_6$ alkoxy" refers to straight chain or branched chain alkoxy groups having from one to six carbon atoms. Illustrative of such alkoxy groups are methoxy, ethoxy, propoxy, isopropoxy, butoxy, isobutoxy, sec-butoxy, t-butoxy, pentoxy, neopentoxy and hexoxy.

As used herein the term "$C_1$-$C_6$ alkylthio" refers to straight chain or branched chain alkylthio groups having from one to six carbon atoms. Illustrative of such alkyl groups are methylthio, ethylthio, propylthio, isopropylthio, butylthio, isobutylthio, sec-butylthio, t-butylthio, pentylthio, neopentylthio and hexylthio.

As used herein, the term "$C_3$-$C_8$ cycloalkyl" refers to an alicyclic group having from 3 to 8 carbon atoms. Illustrative of such cycloalkyl groups are cyclopropyl, cyclobutyl, cyclopentyl and cyclohexyl.

As used herein, the term "$C_4$-$C_8$ cycloalkenyl" refers to an alicyclic group having from 4 to 8 carbon atoms and having in addition one or more double bonds. Illustrative of such cycloalkenyl groups are cyclopentenyl, cyclohexenyl, cycloheptenyl and cyclooctenyl.

As used herein, the term "naturally occurring amino acid" includes alanine. arginine, asparagine, aspartic acid, cysteine cysteine, glutamic acid, glycine, histidine, 5-hydroxylysine, 4-hydroxyproline, isoleucine, leucine, lysine, methionine, phenylalanine, proline, serine, threonine, tryptophan, tyrosine, valine, α-aminoadipic acid, α-amino-n-butyric acid, 3,4-dihydroxyphenylalanine, homoserine, α-methylserine, ornithine, pipecolic acid, and thyroxine. The amino acids may have their side chains protected; for example the carboxyl groups of aspartic acid, glutamic acid and α-aminoadipic acid may be esterified (for example as a —$C_1$-$C_6$ alkyl ester), the amino groups of lysine, ornithine, 5-hydroxylysine, 4-hydroxyproline may be convened to amides (for example as a —CO$C_1$-$C_6$ alkyl amide) or carbamates (for example as a —C(=O)O$C_1$-$C_6$ alkyl or —C(=O)OCH$_2$Ph carbamate), the hydroxyl groups of 5-hydroxylysine, 4-hydroxyproline, serine, threonine, tyrosine, 3,4-dihydroxyphenylalanine, homoserine, α-methylserine and thyroxine may be convened to ethers (for example a —$C_1$-$C_6$ alkyl ether) or esters (for example a —C(=O)$C_1$-$C_6$ alkyl ester) and the thiol group of cysteine may be convened to thioethers (for example a —$C_1$-$C_6$ alkyl thioether) or thioesters (for example a —C(=O)$C_1$-$C_6$ alkyl thioester).

As used herein, the term "nitrogen-containing heterocyclic ring" refers to an aromatic or alicyclic ring comprising one or more nitrogen atoms and optionally one or more other heteroatoms. Illustrative of such rings are pyrrolidine, piperidine, hexamethyleneimine, heptamethylenimine, morpholine and piperazine.

In compounds of this invention, the presence of several asymmetric carbon atoms gives rise to diastereoisomers, each of which consists of two enantiomers, with the appropriate R or S stereochemistry at each chiral center. The invention is understood to include all such diastereoisomers, their optically active enantiomers and mixtures thereof.

The term "pharmaceutically or veterinarily acceptable acid addition salt" refers to a salt prepared by contacting a compound of formula (I) with an acid whose anion is generally considered suitable for human or animal consumption.

Examples of pharmaceutically and/or veterinarily acceptable acid addition salts include the hydrochloride, sulphate, phosphate, acetate, propionate, lactate, maleate, succinate and tartrate salts.

Preferred compounds include those in which, independently or in any compatible combination;

$R^1$ represents a hydrogen atom or a —$C_1$-$C_6$ alkyl (for example methyl) group;

$R^2$ represents a hydrogen atom;

$R^3$ represents a hydrogen atom;

$R^4$ represents a hydrogen atom or a halogen (for example chlorine) atom;

$R^5$ represents a hydrogen atom, a —$C_1$-$C_6$ alkyl (for example methyl or ethyl) group, a —$CO_2C_1$-$C_6$ alkyl (for example ethoxycarbonyl or isobutoxycarbonyl) group, or a —($C_1$-$C_6$alkyl)$CO_2C_1$-$C_6$ alkyl (for example methoxycarbonylmethyl, ethoxycarbonylmethyl or t-butyloxycarbonylmethyl) group;

$R^6$ represents a hydrogen atom;

$R^7$ represents a hydrogen atom, a —$C_1$-$C_6$ alkyl (for example n-propyl) group, a —$C_1$-$C_6$ alkenyl (for example allyl) group, or the side chain of a naturally occurring amino acid (for example the side chain of leucine, isoleucine or valine), wherein the stereochemistry of the carbon atom to which $R^6$ and $R^7$ are attached is the same as, or the opposite to, that of the naturally occurring amino acid;

B represents a $ZR^{11}$ group;

wherein:

Z represents a —C(=O) — group, a —C(=O)O— group, a —($C_1$-$C_6$ alkyl)OC(=O)— (for example —$CH_2OC(=O)$ —) group, a —($C_1$-$C_6$ alkyl)O— (for example —$CH_2O$ — or —CHMeO—) group, a —($C_1$—$C_6$ alkyl)C(=O)O— (for example —$CH_2C(=O)O$—) group, or a —($C_1$-$C_6$ alkyl)OSiPh$_2$— (for example —$CH_2OSiPh_2$—) group;

$R^{11}$ represents a —$C_1$-$C_{18}$ alkyl (for example methyl, ethyl or t-butyl) group, a —$C_2$-$C_{18}$ alkenyl group (for example allyl) or a group D;

n represents an integer of 1;

$R^8$ represents a hydrogen atom;

$R^9$ represents a hydrogen atom;

Particularly preferred compounds include:

1. N-Methyl-N-4-(5H-imidazo[4,5-c]pyridylmethyl)-phenylsulphonyl-L-leucine ethyl ester,
2. N-Methyl-N-4-(5H-2-methylimidazo[4,5-c]pyridylmethyl)phenylsulphonyl-L-leucine ethyl ester.
3. N-Methyl-N-4-(5H-2-methylimidazo[4,5-c]pyridylmethyl)phenylsulphonyl-L-leucine benzyl ester,
4. N-Methyl-N-4-(5H-2-methylimidazo[4,5-c]pyridylmethyl)phenylsulphonyl-L-isoleucine allyl ester,
5. N-Methyl-N-4-(5H-2-methylimidazo[4,5-c]pyridylmethyl)-3-chlorophenylsulphonyl-L-leucine ethyl ester,
6. N-Ethoxycarbonylmethyl-N-4-(5H-2-methylimidazo[4,5-c]pyridylmethyl)phenylsulphonyl-L-leucine ethyl ester,
7. N-Methoxycarbonylmethyl-N-4-(5H-2-methylimidazo[4,5-c]pyridylmethyl)phenylsulphonyl-L-leucine ethyl ester,
8. N-t-Butyloxycarbonylmethyl-N-4-(5H-2-methylimidazo[4,5-c]pyridylmethyl)phenylsulphonyl-L-leucine ethyl ester,
9. N-Ethoxycarbonyl-N-4-(5H-2-methylimidazo[4,5-c]pyridylmethyl)phenylsulphonyl-L-leucine ethyl ester,
10. N-Methyl-N-4-(5H-2-methylimidazo[4,5-c]pyridylmethyl)phenylsulphonyl-$\beta$-alanine ethyl ester.
11. N-Methyl-N-4-(5H-2-methylimidazo[4,5-c]pyridylmethyl)phenylsulphonyl-2-keto-3-amino-4-methylpentane.
12. N-4-(5H-2-Methylimidazo[4,5-c]pyridylmethyl)-phenylsulphonyl-D-leucinyl allyl ether,
13. N-Methyl-N-4-(5H-2-methylimidazo[4,5-c]pyridylmethyl)phenylsulphonyl-D-leucinyl allyl ether,
14. N-4-(5H-2-Methylimidazo[4,5-c]pyridylmethyl)-phenylsulphonyl-L-leucinyl allyl ether,
15. N-Methyl-N-4-(5H-2-methylimidazo[4,5-c]pyridylmethyl)phenylsulphonyl-L-leucinyl allyl ether,
16. N-4-(5H-2-Methylimidazo[4,5-c]pyridylmethyl)-phenylsulphonyl-n-propylglycinyl ethyl ether,
17. N-Ethyl-N-4-(5H-2-methylimidazo[4,5-c]pyridylmethyl)phenylsulphonyl-n-allylglycinyl ethyl ether,
18. N-Ethyl-N-4-(5H-2-methylimidazo[4,5-c]pyridylmethyl)-3-chlorophenylsulphonyl-L-leucinyl ethyl ether,
19. N-Isobutoxycarbonyl-N-4-(5H-2-methylimidazo[4,5-c]pyridylmethyl)phenylsulphonyl-L-leucinyl ethyl ether.
20. N-Ethoxycarbonyl-N-4-(5H-2-methylimidazo[4,5-c]pyridylmethyl)phenylsulphonyl-L-leucinyl ethyl ether,
21. N-Methyl-N-4-(5H-2-methylimidazo[4,5-c]pyridylmethyl)phenylsulphonyl-L-leucinyl t-butyldiphenylsilyl ether,
22. N-4-(5H-2-Methylimidazo[4,5-c]pyridylmethyl)-phenylsulphonyl-L-leucinyl acetate.
23. N-Methyl-N-4-(5H-2-methylimidazo[4,5-c]pyridylmethyl)phenylsulphonyl-2-methoxy-3-amino-4-methylpentane.

Compounds of general formula I may be prepared by any suitable method known in the art and/or by the following process, which itself forms part of the invention.

According to a second aspect of the invention, there is provided a process for preparing a compound of general formula I as defined above, the process comprising:

(a) treating an imidazole derivative represented by general formula II

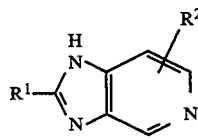

II wherein $R^1$ and $R^2$ are as defined in general formula I, with a suitable base (e.g. sodium hydride, potassium hydride or sodium bis(trimethylsilyl)amide), followed by a compound of general formula III

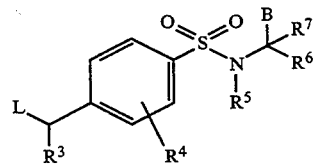

III wherein $R^3$, $R^4$, $R^5$, $R^6$, $R^7$ and B are as defined in general formula I, and L is chloro, bromo, iodo, methanesulphonyloxy, p-toluenesulphonyloxy or trifluoromethanesulphonyloxy; or (b) optionally after step (a) converting, in one or a plurality of steps, a compound of general formula I into another compound of general formula I.

The reaction of step (a) can for preference be conducted in an aprotic solvent, preferably tetrahydrofuran, to yield compounds of general formula I. The reaction yields an isomeric mixture, which is separated by chromatography to yield compounds of general formula I.

By means of step (b) compounds of general formula I wherein B is a —$CO_2NR^{12}R^{13}$ group wherein $R^{12}$ and $R^{13}$ are as defined in general formula I, may be prepared by the following methods:

i) by treatment of a compound of general formula I wherein B is a —$CO_2R^{11}$ group wherein $R^{11}$ is a benzyl group with hydrogen in the presence of a noble metal catalyst (eg 10% palladium on charcoal) to give a carboxylic acid which is then treated with an amine of general formula $HNR^{12}R^{13}$ in the presence of a coupling reagent (e.g. dicyclohexylcarbodiimide);

ii) by treatment of a compound of general formula I wherein B is a —$CO_2R^{11}$ group wherein $R^{11}$ is a lower alkyl with a dimethylaluminium amide of general formula IV $$(Me)_2AlNR^{12}R^{13} \qquad \text{IV}$$

wherein $R^{12}$ and $R^{13}$ are as defined in general formula I, which is prepared in situ from trimethylaluminium and an amine of general formula $HNR^{12}R^{13}$.

Also by means of step (b) compounds of general formula I may be prepared by the treatment of a compound of general formula I wherein $R^5$ is hydrogen with base followed by an electrophile of general formula V $$LR^5 \qquad \text{V}$$

wherein $R^5$ is as defined in general formula I but is not a hydrogen atom, a phenyl or a substituted phenyl group, and L is as defined in general formula III. Electrophiles of general formula V are available in the art or can be prepared by procedures known to those skilled in the art.

Also by means of step (b) certain compounds of general formula I wherein $R^5$ is as defined in general formula I but is not a hydrogen atom, can be prepared by treatment of a compound of general formula I wherein $R^3$ is a hydrogen atom with a suitable base (e.g. sodium bis(trimethylsilyl)amide) in an aprotic solvent (e.g tetrahydrofuran) followed by an electrophile of the general formula $LR^3$ wherein $R_3$ is —$C_1$-$C_6$ alkyl, —$C_3$-$C_6$ alkenyl, —$CO_2C_1$-$C_6$ alkyl, —$SC_1$-$C_6$ alkyl, —($C_1$-$C_6$ alkyl)$SC_1$-$C_6$ alkyl, —($C_1$-$C_6$ alkyl)$OC_1$-$C_6$ alkyl or —($C_1$-$C_6$ alkyl)phenyl and L is chloro, bromo, iodo, methanesulphonyloxy, p-toluenesulphonyloxy or trifluoro-methanesulphonyloxy. Electrophiles of the general formula $LR^3$ are available in the art or can be prepared by methods analogous to those known in the art.

Also by means of step (b) certain compounds of general formula I wherein B is a $ZR^{11}$ group wherein Z is —$CH_2O$— and $R^{11}$ is hydrogen may be prepared by treatment of a compound of general formula I wherein B is a $ZR^{11}$ group wherein Z is —C(=O)O— and $R^{11}$ is other than hydrogen with a suitable reducing agent (e.g. lithium aluminium hydride).

Also by means of step (b) certain compounds of general formula I wherein B is a $ZR^{11}$ group wherein Z is —($C_1$-$C_6$ alkyl)O— and $R^{11}$ is other than hydrogen may be prepared by treatment of a compound of general formula I wherein B is a $ZR^{11}$ group wherein Z is —($C_1$-$C_6$ alkyl)O— and $R^{11}$ is hydrogen with a suitable base in an aprotic solvent followed by an electrophile of general formula $LR^{11}$ wherein $R^{11}$ is as defined in general formula I and L is chloro, bromo, iodo, methanesulphonyloxy, p-toluenesulphonyloxy or trifluoromethanesulphonyloxy. Electrophiles of the general formula $LR^{11}$ are available in the art or can be prepared by methods analogous to those known in the art.

Also by means of step (b) certain compounds of general formula I wherein B is a $ZR^{11}$ group wherein Z is —($C_1$-$C_6$ alkyl)OC(=O) — and $R^{11}$ is other than hydrogen may be prepared by treatment of a compound of general formula I wherein B is a $ZR^{11}$ group wherein Z is —($C_1$-$C_6$ alkyl)O— and $R^{11}$ is hydrogen with a suitable carboxylic acid derivative of general formula $R^{11}C(=O)Q$ wherein Q is a hydrogen, halide or a —O-(O=)$CR^{11}$ group. The conditions for this reaction will depend on the nature of the group Q and will be apparent to one skilled in the art. Carboxylic acids of the general formula $R^{11}C(=O)Q$ are available in the art or can be prepared by methods analogous to those known in the art.

Also by means of step (b) certain compounds of general formula I wherein B is a $ZR^{11}$ group wherein Z is —($C_1$-$C_6$ alkyl)OC(=O)NH — and $R^{11}$ is other than hydrogen may be prepared by treatment of a compound of general formula I wherein B is a $ZR^{11}$ group wherein Z is —($C_1$-$C_6$ alkyl)O— and $R^{11}$ is hydrogen with an isocyanate of general formula $R^{11}$—N=C=O. Isocyanates of the general formula $R^{11}$—N=C=O are available in the art or can be prepared by methods analogous to those known in the art.

Imidazole derivatives of general formula II may be prepared by a number of methods. The first method involves treatment of a 1,2-diamine of general formula VI

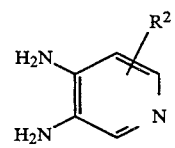

wherein $R^2$ is as defined in general formula I, with dimethylformamide and a carboxylic acid of general formula VII $$R^1CO_2H \qquad \text{VII}$$

wherein $R^1$ is as defined in general formula I. Derivatives of carboxylic acids of general formula VII, such as acid halides of general formula VIII $$OOCR^1 \qquad \text{VIII}$$

wherein $R^1$ is as defined in general formula I and X is fluoride, chloride, bromide or iodide, in an aprotic solvent and in the presence of a suitable base such as, for example, triethylamine, may alternatively be used.

Alternatively, the reaction may be conducted utilising an acid anhydride of general formula IX

  IX wherein R¹ is as defined in general formula I, utilising trialkylorthoesters of general formula X

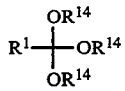  X wherein R¹ is as defined in general formula I and R¹⁴ is —C₁-C₆ alkyl or utilising imino ether salts of general formula XI

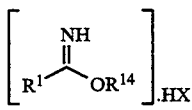  XI wherein R¹ is as defined in general formula I, R¹⁴ is —C₁-C₆ alkyl and X is fluoride, chlorid, bromide, or iodide. Carboxylic acids of general formula VII, acid halides of general formula VIII, acid anhydrides of general formula IX, trialkylorthoesters of general formula X and imino ether salts of general formula XI are available in the art or can be prepared by methods analogous to those known in the art.

1,2-Diamines of general formula VI are available in the art or may be prepared by the reduction of a 1,2-nitroamine of general formula XII

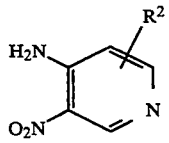  XII wherein R² is as defined in general formula I, for example in the presence of hydrogen and a catalyst such as palladium or platinum.

1,2-Nitroamines of general formula XII are available in the art or can be prepared by methods analogous to those known in the art.

In a second method imidazole derivatives of general formula II may be prepared by the treatment of an 1,2-nitroamide of general formula XIII

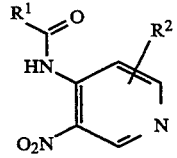  XIII wherein R¹ and R² are as defined in general formula I, with a suitable reducing agent (e.g. tin in acetic acid).

1,2-Nitroamides of general formula XIII may be prepared by the treatment of a 1,2-nitroamine of general formula XII with an acid halide of general formula VIII, wherein R¹ is as defined in general formula I, in an aprotic solvent and in the presence of a suitable base such as, for example, triethylamine. Alternatively, the reaction may be conducted utilising an acid anhydride of general formula IX wherein R¹ is as defined in general formula I.

Another procedure for preparing 1,2-nitroamides of general formula XIII involves reaction of a 1,2-nitroamine of general formula XII with a carboxylic acid of general formula VII, wherein R¹ is as defined in general formula I, in the presence of a coupling reagent (e.g. 1,3-dicyclohexylcarbodiimide).

Compounds of general formula III may be prepared by treatment of an amine of general formula XIV

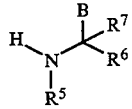  XIV wherein R³, R⁶, R⁷, and B are as defined in general formula I, with a sulphonyl halide of general formula XV

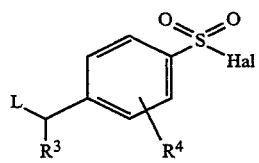  XV wherein R³ and R⁴ is as defined in general formula I, L is as defined in general formula III and Hal is a halide (e.g. fluoro, chloro or bromo), in the presence of a suitable base (e.g. triethylamine). Amines of general formula XIV and sulphonyl halides of general formula XV are known in the art or may be prepared by methods known in the art.

The appropriate solvents employed in the above reactions are solvents wherein the reactants are soluble but do not react with the reactants. The preferred solvents vary from reaction to reaction and are readily ascertained by one of ordinary skill in the art.

The compound of general formula III is a valuable intermediate in the preparation of compounds of general formula I, as are other novel compounds specifically or generically disclosed herein. According to a third aspect of the invention, there is therefore provided a compound of general formula III.

This invention also relates to a method of treatment for patients (or animals including mammalian animals raised in the dairy, meat, or fur trade or as pets) suffering from disorders or diseases which can be attributed to PAF as previously described, and more specifically, a method of treatment involving the administration of PAF antagonists of general formula I as the active ingredient. In addition to the treatment of warm blooded animals such as mice, rats, horses, cattle, pigs, sheep, dogs, cats, etc., the compounds of the invention are effective in the treatment of humans.

According to a fourth aspect of the invention there is provided a compound of general formula I for use in human or veterinary medicine particularly in the management of diseases mediated by PAF; compounds of general formula I can be used among other things to reduce inflammation and pain, to correct respiratory, cardiovascular, and intravascular alterations or disorders, and to regulate the activation or coagulation of platelets, to correct hypotension during shock, the pathogenesis of immune complex deposition and smooth muscle contractions.

According to an fifth aspect of the invention there is provided the use of a compound of general formula I in the preparation of an agent for the treatment or prophylaxis of PAF-mediated diseases, and/or the treatment of inflammatory disorders; such as rheumatoid arthritis, osteoarthfitis and eye inflammation. cardiovascular disorder, thrombocytopenia, asthma, endotoxin shock, adult respiratory distress syndrome, glomerulonephritis, immune regulation, gastric ulceration, transplant rejection, psoriasis, allergic dermatitis, urticaria, multiple sclerosis, cerebral, myocardial and renal ischemia and any other condition in which PAF is implicated.

Compounds of general formula (I) may be administered orally, topically, parenterally, by inhalation spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques.

According to an sixth aspect of the invention there is provided a pharmaceutical or veterinary formulation comprising a compound of general formula I and a pharmaceutically and/or veterinarily acceptable carrier. One or more compounds of general formula I may be present in association with one or more non-toxic pharmaceutically and/or veterinarily acceptable carriers and/or diluents and/or adjuvants and if desired other active ingredients.

The pharmaceutical compositions containing compounds of general formula I may be in a form suitable for oral use, for example, as tablets, troches, lozenges, aqueous or oily suspensions dispersible powders or granules, emulsion, hard or soft capsules, or syrups or elixirs.

Compositions intended for oral use may be prepared according to any method known to the art for the manufacture of pharmaceutical compositions and such compositions may contain one or more agents selected from the group consisting of sweetening agents, flavouring agents, colouring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid: binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxypropylmethylcellulose, sodium alginate, polyvinylpyrrolidone, gum tragacanth and gum acacia; dispersing or wetting agents may be a naturallyoccuring phosphatide, for example lecithin, or condensation products of an alkylene oxide with fatty acids for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydfides, for example polyethylene sorbitan monooleate. The aqueous suspensions may also contain one or more preservatives, for example ethyl, or n-propyl p-hydroxybenzoate, one or more colouring agents, one or more fiavouring agents, and one or more sweetening agents, such as sucrose or saccharin.

Oily suspensions may be formulated by suspending the active ingredients in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavouring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavouring and colouring agents, may also be present.

Pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth naturally-occurring phosphatides for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavouring agents.

Syrups and elixirs may be formulated with sweetening agents, for example glycerol, propylene glycol, sorbitol or sucrose. Such formulations may also contain a demulcent, a preservative and flavouring and colouring agents. The pharmaceutical compositions may be in the form of a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parentally acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of general formula I may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical application to the skin compounds of general formula I may be made up into a cream, ointment, jelly, solution or suspension etc. Cream or ointment formulations that may be used for the drug are conventional formulations well known in the art, for example, as described in standard text books of pharmaceutics such as the British Pharmacopoeia.

For topical applications to the eye, compounds of general formula I may be made up into a solution or suspension in a suitable sterile aqueous or non-aqueous vehicle. Additives, for instance buffers, preservatives including bactericidal and fungicidal agents, such as phenyl mercuric acetate or nitrate, benzalkonium chloride or chlorohexidine, and thickening agents such as hypromellose may also be included.

Compounds of general formula I may be administered parenterally in a sterile medium. The drug depending on the vehicle and concentration used, can either be suspended or dissolved in the vehicle. Advantageously, adjuvants such as a local anaesthetic, preservative and buffering agents can be dissolved in the vehicle.

Compounds of general formula I may be used for the treatment of the respiratory tract by nasal or buccal administration of, for example, aerosols or sprays which can disperse the pharmacological active ingredient in the form of a powder or in the form of drops of a solution or suspension. Pharmaceutical compositions with powder-dispersing properties usually contain, in addition to the active ingredient, a liquid propellant with a boiling point below room temperature and, if desired, adjuncts, such as liquid or solid non-ionic or anionic surfactants and/or diluents. Pharmaceutical compositions in which the pharmacological active ingredient is in solution contain, in addition to this, a suitable propellant, and furthermore, if necessary, an additional solvent and/or a stabiliser. Instead of the propellant, compressed air can also be used, it being possible for this to be produced as required by means of a suitable compression and expansion device.

Dosage levels of the order of from about 0.1 mg to about 140 mg per kilogram of body weight per day are useful in the treatment of the above-indicated conditions (about 0.5 mg to about 7 g, per patient per day). For example, inflammation may be effectively treated by the administration of from about 0.01 to 50 mg of the compound per kilogram of body weight per day (about 1.0 mg to about 3.5 g per patient per day). The dosage employed for the topical administration will, of course, depend on the size of the area being treated. For the eyes each dose will be typically in the range from 10 to 100 mg of the drug.

The amount of active ingredient that may be combined with the carrier materials to produce a single dosage form will vary depending upon the host treated and the particular mode of administration. For example, a formulation intended the oral administration of humans may contain from 0.5 mg to 5 g of active agent compounded with an appropriate and convenient amount or carrier material which may vary from about 5 to about 95 percent of the total composition. Dosage unit forms will generally contain between from about 1 mg to about 500 mg of an active ingredient.

It will be understood, however, that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy.

It has been found that the compounds of general formula I exhibit in vitro antagonistic activities with respect to PAF. Compounds of general formula I inhibit PAF-induced functions in both the cellular and tissue levels by changing the PAF binding to its specific receptor site. The ability of compounds of general formula I to inhibit the binding of PAF to its specific receptor binding site on human platelet plasma membranes was measured according to Example 24.

The following examples illustrate the invention, but are not intended to limit the scope in any way.

The following abbreviations have been used in the Examples:
DCM-Dichloromethane
DIPE-Diisopropylether
DMAP-4-Dimethylaminopyridine
DMF-Dimethylformamide
NBS-N-Bromosuccinimide
TDA-1-Tris(2-(2-methoxyethoxy)ethyl)amine
THF-Tetrahydrofuran
TLC-Thin layer chromatography
MPLC-Medium pressure liquid chromatography Unless otherwise stated $^1$H NMR and $^{13}$C NMR spectra were recorded on a Bruker AC-250 spectrometer at 250 MHz and 62.9 MHz respectively using CDCl$_3$ as solvent and internal reference and are reported as delta ppm from TMS.

EXAMPLE 1

N-Methyl-N-4-(5H-imidazo[4,5-c]pyridylmethyl)-phenylsulphonyl-L-leucine ethyl ester

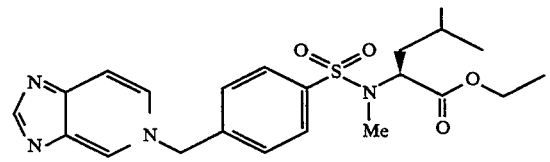

(a) 4-Bromomethylphenylsulphonyl chloride

To a solution of p-toluenesulphonyl chloride (50 g, 0.26 mol) in benzene (150 ml) and NBS (46.7 g, 0.26 mol) heated at reflux was added 2,2'-azobis(2-methylpropionitrile) (100 mg). The mixture was heated at reflux for 12 h and allowed to cool to room temperature. The white precipitate of succinimide that formed was separated and discarded. The flitrate was taken up in DCM (200 ml) and washed with water (3×100 ml) followed by brine (100 ml) and dried over anhydrous sodium sulphate. Filtration, concentration and subsequent crystallisation (from DIPE) gave in two crops 4-bromomethylphenylsulphonyl chloride as a white crystalline solid (46.3 g, 66%).

delta$_H$ 8.02 (2H, d, J 8.5 Hz), 7.64 (2H, d, J 8.5 Hz), 4,52 (2H, s).

(b) N-4-Bromomethylphenylsulphonyl-L-leucine ethyl ester

L-Leucine ethyl ester hydrochloride (75.0 g, 0.403 mol) was suspended in THF at 0° C., and triethylamine (67 ml, 0.484 mol) added slowly. After stirring for 15 mins a solution of 4-bromomethylphenylsulphonyl chloride (108.4 g, 0.403 mol) in THF (100 ml) was added via cannular. The reaction mixture was allowed to stir overnight at ambient temperature. The solvent was removed under reduced pressure and the organics were extracted into ethyl acetate (200 ml) and washed with water (100 ml) and brine (100 ml). The organic portion was dried over anhydrous magnesium sulphate and the solvent evaporated under reduced pressure. The product was recrystallised from DIPE (500 ml) to give N-4-bromomethylphenylsulphonyl-L-leucine ethyl ester (104 g, 82%) as a white crystalline solid.

delta$_H$ 7.84 (2H, d, J 8.3 Hz), 7.52 (2H, d, J 8.3 Hz), 5.06 (1H, d, J 10.1 Hz), 4.61 (2H, s), 3.97-3.82 (3H, m), 1.85-1.79 (1H, m), 1.49 (2H, t, J 7.1 Hz), 1.08(3H, t, J 7.1 Hz), 0.92 (3H, d, J 6.7 Hz), 0.91 (3H, d, J 6.5 Hz).

(c) N-Methyl-4-bromomethylphenylsulphonyl-L-leucine ethyl ester

To a solution of N-4-bromomethylphenylsulphonyl-L-leucine ethyl ester (10.0 g, 25.4 mmol) in THF (100 ml) was added sodium hydride (1.1 g of a 60% dispersion in oil, 27.94 mmol) and the mixture stirred at room temperature. The mixture was cooled to 0° C. and methyl iodide (4.8 ml, 76.2 mmol) added and the reaction allowed to warm to room temperature overnight. The solvent was removed by evaporation, the residue taken up in ethyl acetate, and washed with aqueous ammonium chloride, water (100 ml), brine (100 ml) and dried over anhydrous magnesium sulphate. Removal of solvent by evaporation under reduced pressure yielded N-methyl-N-4-bromomethylphenylsulphonyl-L-leucine ethyl ester as an orange oil which was used directly in the next step without further purification.

(d) N-Methyl-N-4-(5H-2-imidazo[4,5-c]pyridylmethyl)phenylsulphonyl-L-leucine ethyl ester Imidazo[4,5-c]pyridine (6.8 g, 15 mmol) was dissolved in dry acetonitrile (200 ml) at room temperature Potassium hydroxide (0.86 g, 15 mmol) and TDA-1 (few drops) were added and the reaction mixture heated to 80° C. for 2 hours. The resuting mixture was cooled to 40° C. and a solution of N-methyl-N-4-bromomethyl-phenylsulphonyl-L-leucine ethyl ester (6.21 g, 5 mmol) in dry acetonitrile (100 ml) was added. The reaction mixture was heated to 80° C. overnight and then allowed to cool to room temperature. Concentration under reduced pressure, purification by flash chromatography over silica gel (5% methanol in DCM) and crystallisation from ethyl acetate afforded N-methyl-N-4-(5H-imidazo[4,5-c]pyridylmethyl)phenylsulphonyl-L-leucine ethyl ester (0.90 g, 13%) as a white crystalline solid.

m.p. 66° C.

i.r. (CDCl$_3$) 2980, 2200, 1730, 1620, 1400 cm$^1$;

delta$_H$ 8.51 (1H, s), 8.27 (1H, s), 7.51 (1H, d, J 6.8 Hz), 7.42-7.27 (3H, m,), 7.01 (2H, d, 8.3 Hz), 5.35 (2H, s), 4.29 (1H, t, J 6.7 Hz), 3.52-3.40 (2H, m), 2.49 (3H, s), 1.65-1.20 (3H, m), 0.65-0.53 (9H, m).

delta$_C$ 169.8, 163.52, 154.47, 143.64, 138.90, 138.79, 131.16, 129.28, 127.36, 127.28, 112.97, 61.07, 60.22, 56.55, 37.19, 29.13, 23.61, 22.25, 20.29, 13.11.

EXAMPLE 2

N-Methyl-N-4-(5H-2-methylimidazo[4,5-c]pyridylmethyl)phenylsulphonyl-L-leucine ethyl ester

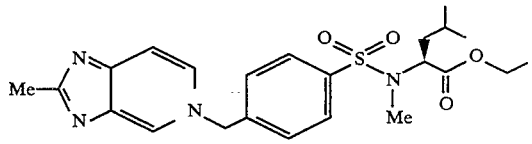

N-Methyl-N-4-(5H-2-methylimidazo[4,5-c]pyridylmethyl)phenylsUlphonyl-L-leucine ethyl ester was prepared by the method described in Example 1 employing 2-methylimidazo[4,5-c]pyridine in lieu of imidazo[4,5-c]pyridine in Step (d).

White foam (8% yield for last step after chromatography over silica gel (5% methanol in DCM)).

i.r. (CDCl$_3$) 2200, 1730, 1325, 1145 cm$^{-1}$;

delta$_H$ 8.60 (1H, s), 7.77 (1H, d, J 6.7 Hz), 7.48-7.38 (3H, m), 7.18 (2H, d, J 8.1 Hz), 5.56 (2H, s), 4.34 (1H, m), 3.62-3.50 (2H, m), 2.54 (3H, s), 2.46 (3H, s), 1.39-1.25 (3H, m), 0.79-0.61 (9H, m).

delta$_C$ 171.89, 170.04, 154.14, 143.52, 139.07, 138.84, 130.89, 129.59, 127.63. 127.49, 111.36, 61.12, 60.40, 56.65, 37.31, 29.23, 23.72, 22.38, 20.41, 17.25. 13.30.

EXAMPLE 3

N-Methyl-N-4-(5H-2-methylimidazo[4,5-c]pyridylmethyl)phenylsulphonyl-L-leucine benzyl ester

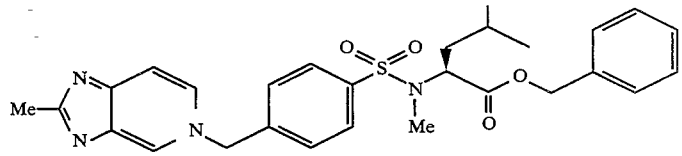

A stirred solution of 2-methylimidazo[4,5-c]pyridine (1.36 g, 10 mmol) in dry THF (60 ml) at room temperature was treated with sodium hydride (0.41 g of 60% dispersion in oil, 10 mmol). The reaction mixture was stirred at room temperature for 20 minutes and then cooled to 0° C. N-Methyl-N-4-bromomethylphenylsulphonyl-L-leucine benzyl ester (4.8 g, 10 mmol)(prepared by the method of Example 1 Steps (b) and (c) starting from L-leucine benzyl ester) in dry THF (40 ml) was added and the reaction mixture allowed to warm to room temperature overnight. The resulting mixture was treated with a mixture of ethyl acetate and brine, the organic layer was separated, dried over anhydrous sodium sulphate, filtered, and concentrated under reduced pressure. Purification of the residue by chromatography over silica gel (6% methanol in DCM) afforded N-methyl-N-4-(5H-2-methylimidazo[4,5c-

]pyridylmethyl)phenyl-sulphonyl-L-leucine benzyl ester (0.3 g, 6%) as a pale yellow oil.

i.r. (KBr) 1730, 1320, 1145 cm$^{-1}$;

delta$_H$ 8.34 (1H, s), 7.68 (2H, d, J 8.5 Hz), 7.60–7.50 (2H, m), 7.30–7.20 (3H, m), 7.19–7.00 (4H, m), 5.44 (2H, s), 4.90 (1H, d, J 12.4 Hz), 4.82 (1H, d, J 12.4 Hz), 4.77–4.67 (1H, m), 2.77 (3H, s), 2.73 (3H, s), 1.65–1.55 (3H, m), 0.96–0.89 (6H, m).

EXAMPLE 4

N-Methyl-N-4-(5H-2-methylimidazo[4,5-c]pyridylmethyl)phenylsulphonyl-L-isoleucine allyl ester

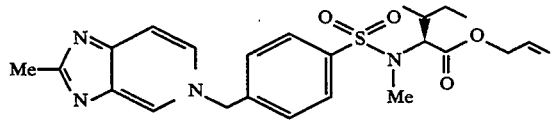

N-Methyl-N-4-(5H-2-methylimidazo[4,5-c]pyridylmethyl)phenylsulphonyl-L-isoleucine allyl ester was prepared by the procedure of Example 3 employing N-methyl-N-4-bromomethylphenylsulphonyl-L-isoleucine allyl ester (prepared by the method of Example 1 Steps (b) and (c) starting from L-isoleucine allyl ester hydrochloride) in lieu of N-methyl-N-4-bromomethylphenylsulphonyl-L-leucine benzyl ester.

Colourless oil (purified by chromatography over silica gel (5% methanol in DCM)):

i.r. (CDCl$_3$) 1730, 1330, 1150 cm$^{-1}$;

delta$_H$ 8.32 (1H, d, J 1.0 Hz), 7.63–7.44 (4H, m), 7.11 (2H, d, J 8.3 Hz), 5.60–5.42 (1H, m), 5.43 (2H, s), 5.05–4.92 (2H, m), 4.23–4.00 (3H, m); 2.73 (3H, s), 2.63 (3H, s), 1.85–1.70 (1H, m), 1.53–1.36 (1H, m), 1.10–0.92 (1H, m), 0.85–0.70 (6H, m);

delta$_C$ 175.19, 169.28, 156.36, 145.39, 139.14, 130.77, 129.57, 128.68, 127.96, 127.33, 118.66, 111.81, 64.90, 63.29, 61.54, 33.39, 29.92, 24.67, 16.14, 14.98, 10.10.

EXAMPLE 5

N-Methyl-N-4-(5H-2-methylimidazo[4,5-c]pyridylmethyl)-3-chlorophenylsulphonyl-L-leucine ethyl ester

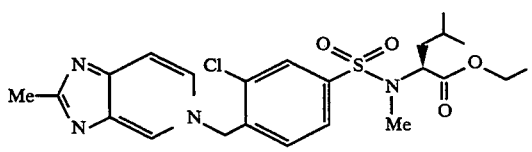

(a) 3-chloro-4-bromomethylphenylsulphonyl chloride

NBS (13.76 g, 76 mmol) was added to a stirred solution of 3-chloro-4-methylphenylsulphonyl chloride (12 g, 76 mmol) in CCl$_4$ (120 ml) under argon.

After one hour benzoyl peroxide (0.92 g, 3.8 mmol) was added and the reaction mixture refluxed overnight. The mixture was allowed to cool, the resulting white precipitate filtered off and the filtrate evaporated to a yellow oil. Purification of the residue by chromatography over silica gel (3% ethyl acetate in hexane) afforded 3-chloro-4-bromomethylphenylsulphonyl chloride (3.3 g, 14%);

delta$_H$ 8.27 (1H, d, 9.4 Hz), 8.06–7.98 (3H, m), 7.96–7.90 (1H, m), 7.72 (1H, d, J 9.4 Hz), 7.06 (1H, s), 4.62 (2H, s).

(b) N-3-Chloro-4-bromomethylphenylsulphonyl-L-leucine ethyl ester

N-3-Chloro-4-bromomethylphenylsulphonyl-L-leucine ethyl ester was prepared following the procedure of Example 1 Step (b) utilising 3-chloro-4-bromomethylphenylsulphonyl chloride in lieu of 4-bromomethylphenylsulphonyl chloride.

Colourless oil (20% yield after purification by chromatography over silica gel (14% ethyl acetate in hexane));

delta$_H$ 7.88 (1H, d, J 3.0 Hz), 7.77–7.72 (1H, m), 7.62 (1H, d, J 8.2 Hz), 5.40 (1H, d, J 9.4 Hz), 4.71 (2H, s), 4.04–3.84 (3H, m), 1.90–1.71 (1H, m), 1.60–1.46 (2H, m), 1.17–1.09 (3H, m), 0.93 (6H, m).

(c) N-Methyl-N-3-chloro-4-bromomethylphenylsulphonyl-L-leucine ethyl ester

N-Methyl-N-3-chloro-4-bromomethylphenylsulphonyl-Leucine ethyl ester was prepared following the procedure of Example 1 Step (c), utilising N-3-chloro-4-bromomethylphenylsulphonyl-L-leucine ethyl ester in lieu of N-4-bromomethylphenylsulphonyl-L-leucine ethyl ester, as an oil which was used directly in the next step.

(d) N-Methyl-N-4-(5H-2-methylimidazo[4,5-c]pyridylmethyl)-3-chlorophenylsulphonyl-L-leucine ethyl ester N-Methyl-N-4-(5H-2-Methylimidazo[4,5-c]pyridylmethyl)- 3-chlorophenyl-sulphonyl-L-leucine ethyl ester was prepared by the method described in Example 3 utilising N-methyl-N-3-chloro-4-bromomethylphenylsulphonyl-L-leucine ethyl ester in lieu of N-methyl-N-4-bromomethylphenylsulphonyl-L-leucine benzyl ester.

Colourless oil (6% yield after purification by chromatography over silica gel (6% methanol in DCM)).

Analysis for C$_{23}$H$_{29}$ClN$_4$O$_4$S Requires C 56.08 H 5.94 N 11.38 Found C 55.70 H 5.99 N 11.16 i.r. (CDCl$_3$) 1735, 1320 cm$^{-1}$;

delta$_H$ 8.42 (1H, s), 7.90 (1H, d, J 1.8 Hz), 7.71–7.62 (3H, m), 7.06 (1H, d, J 8.1 Hz), 5.63 (2H, s), 4.70–4.64 (1H, m), 3.91 (2H, q, J 7.2 Hz), 2.82 (3H, s), 2.76 (3H, s), 1.70–1.59 (3H, m), 1.06 (3H, t, J 7.0 Hz), 1.04–0.93 (6H, m).

EXAMPLE 6

N-Ethoxycarbonylmethyl-N-4-(5H-2-methylimidazo[4,5-c]pyridylmethyl)phenylsulphonyl-L-leucine ethyl ester

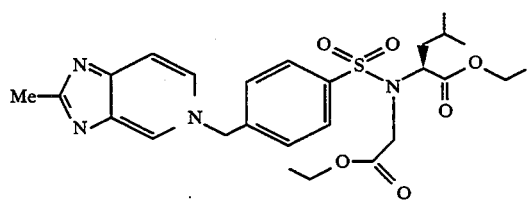

(a) N-Ethoxycarbonylmethyl-N-4-bromomethylphenylsulphonyl-L-leucine ethyl ester

N-4-Bromomethylphenylsulphonyl-L-leucine ethyl ester (2.0 g, 5.1 mmol) was dissolved in THF (50 ml) and the stirred solution was treated with potassium hydride (35% dispersion in oil, 0.583 g). After 20 mins ethyl bromoacetate (1.70 g, 10.2 mmol) was added and the resulting mixture allowed to stir overnight. Ethyl acetate and brine were added, and the organic layer was separated dried over anhydrous magnesium sulphate, filtered and concentrated under reduced pressure. Purification of the residue by chromatography on silica gel (25% ethyl acetate in hexane) afforded N-ethoxycarbonylmethyl-N-4-bromomethylphenylsulphonyl-L-leucine ethyl ester (1.89 g, 77%) as a colourless oil.

delta$_H$ 7.91 (2H, d, J 8.3 Hz), 7.52 (2H, d, J 8.2 Hz), 4.61, 4.49 (2H, 2s), 4.38, (1H, br t, J 7.2 Hz), 4.28–4.03 (4H, m), 3.92 (2H, q, J 7.1 Hz), 1.90–1.70 (1H, m), 1.60–1.48 (2H, m), 1.40–1.22 (3H, m), 1.10 (3H, t, J 7.0 Hz), 0.88 (3H, d, J 6.6 Hz), 0.84 (3H, d, J 6.6 Hz).

(b) N-Ethoxycarbonylmethyl-N-4-(5H-2-methylimidazo[4,5-c]pyridylmethyl)phenylsulphonyl-L-leucine ethyl ester N-Ethoxycarbonylmethyl-N-4-(5H-2-methylimidazo[4,5-c]pyridylmethyl)phenylsulphonyl-L-leucine ethyl ester was prepared by the procedure described in Example 1 Step (d) utilising N-ethoxycarbonylmethyl-N-4-bromomethylphenylsulphonyl-L-leucine ethyl ester in lieu of N-methyl-N-4-bromomethyl-phenylsulphonyl-L-leucine ethyl ester and 2-methylimidazo[4,5-c]pyridine in lieu of imidazo[4,5-c]pyridine.

Yellow foam (19% yield after chromatography over silica gel (5% methanol in DCM));

Analysis for C$_{26}$H$_{34}$N$_4$O$_6$S.1.6H$_2$O Requires C 55.82 H 6.70 N 10.01 Found C 55.74 H 6.41 N 9.74 i.r. (CDCl$_3$) 3690, 2960, 1735, 1625, 1435, 1340, 1315, 1155 cm$^{-1}$;

delta$_H$ 8.37, (1H, s), 7.83 (2H, d, J 5.8 Hz), 7.61–7.57 (2H, m), 7.23 (2H, d, Hz), 5.50 (2H, s), 4.28–3.31 (7H, m), 2.68 (3H, d, J 1.2 Hz), 1.70–1.62 (1H, m), 1.49–1.38 (2H, m), 1.19 (3H, dt, J 7.0, 1.2 Hz), 0.95 (3H, dt, J 7.0, 1.7 Hz), 0.78 (3H, d, J 6.4 Hz), 0.73 (3H, d, J 6.4 Hz);

EXAMPLE 7

N-Methoxycarbonylmethyl-N-4-(5H-2-methylimidazo[4,5-c]pyridylmethyl)phenylsulphonyl-L-leucine ethyl ester

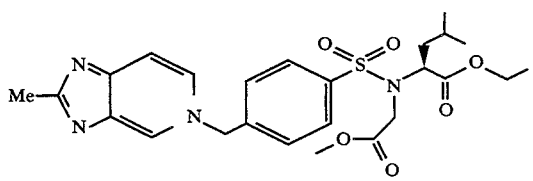

N-Methoxycarbonylmethyl-N-4-(5H-2-methylimidazo[4,5-c]pyridylmethyl)phenylsulphonyl-L-leucine ethyl ester was prepared by the method of Example 6 employing methyl bromoacetate in lieu of ethyl bromoacetate.

White foam (27% yield for last step after chromatography over silica gel (5% methanol in DCM)):

Analysis for C$_{25}$H$_{32}$N$_4$O$_6$S.1.3H$_2$O Requires C 55.60 H 6.46 N 10.37 Found C 55.55 H 6.33 N 10.45 i.r. (CDCl$_3$) 3670, 2960, 2200, 1735, 1630, 1435, 1315, 1155 cm$^{-1}$;

delta$_H$ 8.45 (1H, s), 7.94 (2H, d, J 8.3 Hz), 7.68–7.61 (2H, m), 7.31 (2H, d, J 8.3 Hz), 5.56 (2H, s), 4.32 (1H, dd, J 8.3, 6.4 Hz), 4.22 (1H, d, J 18.5 Hz), 4.08 (1H, d, J 18.5 Hz), 3.90 (2H, dq, J 7.2, 1.0 Hz), 3.71 (3H, s), 2.76 (3H, s), 1.77–1.66 (1H, m), 1.61–1.44 (2H, m), 1.04 (3H, t, J 7.1 Hz), 0.85 (3H, d, J 6.6 Hz), 0.79 (3H, d, J 6.4 Hz).

EXAMPLE 8

N-t-Butyloxycarbonylmethyl-N-4-(5H-2-methylimidazo[4,5-c]pyridylmethyl)phenylsulphonyl-L-leucine ethyl ester

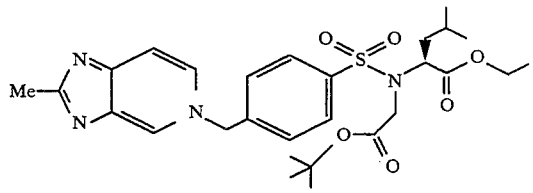

(a) N-t-Butyloxycarbonylmethyl-4-bromomethyl-phenylsulphonyl-L-leucine ethyl ester N-4-Bromomethyphenylsulphonyl-L-leucine ethyl ester (1.0 g, 2.6 mmol) was dissolved in THF (50 ml) and the resulting solution cooled to 0° C. and treated with potassium bis(trimethylsilyl)amide (0.5M in THF, 5 ml) with stirring. The reaction mixture was stirred for 15 rain, treated with t-butyl bromoacetate (0.75 ml, 0.51 mmol) and allowed to warm to room temperature overnight. The reaction mixture was then diluted with ethyl acetate and washed with brine. The organic layer was dried over anhydrous magnesium sulphate, filtered and concentrated under reduced pressure. Purification of the residue by flash chromatography over silica gel (15% ethyl acetate in hexane) afforded N-t-butyloxycarbonylmethyl-4-bromomethylphenylsulphonyl-L-leucine ethyl ester (0.8 g, 54%) as a colourless oil.

delta$_H$ 7.89 (2H, d, J 8.2 Hz), 7.50 (2H, d, J 8.3 Hz), 4.60 (2H, s), 4.39–4.30 (1H, m), 4.11 (1H, d, J 18.5 Hz), 3.96 (1H, d, J 18.5 Hz), 3.90 (2H, q, J 7.1 Hz), 1.90–1.73 (1H, m), 1.60–1.39 (2H, m), 1.47 (9H, s) 1.08 (3H, t, J 7.0 Hz), 0.88 (3H, d, J6.7 Hz), 0.83 (3H, d, J 6.5 Hz).

(b) N-t-Butyloxycarbonylmethyl-N-4-(5H-2-methylimidazo[4,5-c]pyridylmethyl)phenylsulphonyl-L-leucine ethyl ester N-t-Butyloxycarbonylmethyl-N-4-(5H-2-methylimidazo[4,5-c]pyridylmethyl)phenylsulphonyl-L-leucine ethyl ester was prepared by the procedure described in Example 1(d) utilising N-t-butyloxycarbonylmethyl-4-bromomethylphenylsulphonyl-L-leucine ethyl ester in lieu of N-methyl-N-4-bromomethyl-phenylsulphonyl-L-leucine ethyl ester and 2-methylimidazo[4,5-c]pyridine in lieu of imidazo[4,5-c]pyridine.

Pale yellow solid (11% yield after chromatography over silica gel (5% methanol in DCM)): m.p. 74° C.

i.r. (CDCl$_3$) 2190, 1735, 1315 cm$^{-1}$;

delta$_H$ 8.22 (1H, s), 7.53 (2H, d, J 8.3 Hz), 7.45 (1H, d, J 6.7 Hz), 7.27 (1H, d, J 6.7 Hz), 7.01 (2H, d, J 8.3 Hz), 5.31 (2H, s), 3.99 (1H, br t, J 8.2 Hz), 3.80 (1H, d, J 18.5 Hz), 3.64 (1H, d, J 18.5 Hz), 3.53–3.43 (2H, m), 2.53 (3H, s), 1.53–1.38 (1H, m), 1.29–1.12 (11H, m), 0.65 (3H, t, J 7.2 Hz), 0.53 (3H, d, J 6.6 Hz), 0.48 (3H, d, J 6.5 Hz);

delta$_C$ 174.61, 170.03, 167.70, 156.07, 145.15, 139.44, 139.23, 129.37, 128.44, 128.03, 127.17, 111.31, 81.23, 61.08, 60.50, 56.90, 45.73, 38.79, 27.26, 23.41, 21.91, 20.82, 17.89, 13.20.

EXAMPLE 9

N-Ethoxycarbonyl-N-4-(5H-2-methylimidazo[4,5-c]pyridylmethyl)phenylsulphonyl-L-leucine ethyl ester

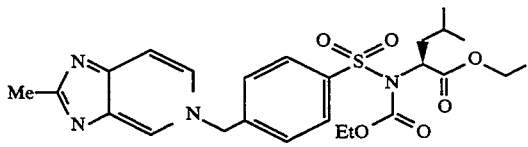

(a) N-Ethoxycarbonyl-N-4-bromomethylphenylsulphonyl-L-leucine ethyl ester

A solution of sodium bis(trimethylsilyl)amide (1M in THF, 39 ml, 39 mmol ) was added to a stirred solution of N-4-bromomethylphenylsulphonyl-L-leucine ethyl ester (15.0 g, 38.2 mmol) in dry THF (150 ml) at room temperature under argon. The reaction mixture was cooled to 0° C. and ethyl chloroformate (3.7 ml, 38.3 mmol) was added. The mixture was allowed to warm to room temperature and was stirred overnight. The solvent was removed under reduced pressure and the residue taken up in ethyl acetate (150 ml) and aqueous ammonium chloride (100 ml) added. The organic layer was separated, washed with brine (100 ml). dried over anhydrous sodium sulphate, filtered and concentrated under reduced pressure. The residue was purified by chromatography (silica: 15% ethyl acetate in hexane) to give N-ethoxycarbonyl-N-4-bromomethylphenylsulphonyl-L-leucine ethyl ester (6.1 g, 34%) as a colourless oil.

delta$_H$ 8.06 (2H, d, J 8.4 Hz), 7.55 (2H, d, J 8.4 Hz), 5.14 (1H, dd, J 8.6, 5.6 Hz) 4.63 (3H, s), 4.22–4.03 (4H, m), 2.07–1.97 (2H, m), 1.78 (1H, m), 1.20 (3H, t, J 7.1 Hz), 1.10 (3H, t, J 7.2 Hz), 1.05 (3H, d, J 6.4 Hz), 1.00 (3H, d, J 6.4 Hz).

(b) N-Ethoxycarbonyl-N-4-(5H-2-methylimidazo[4,5-c]pyridylmethyl)phenylsulphonyl-L-leucine ethyl ester N-Ethoxycarbonyl-N-4-(5H-2-methylimidazo[4,5-c]pyridylmethyl)phenylsulphonyl-L-leucine ethyl ester was prepared by the procedure described in Example 1 Step (d) utilising N-ethoxycarbonyl-N-4-bromomethylphenylsulphonyl-L-leucine ethyl ester in lieu of N-4-bromomethylphenylsulphonyl-L-leucine ethyl ester and 2-methylimidazo[4,5-c]pyridine in lieu of imidazo[4,5-c]pyridine.

White foam (4% yield for last step after chromatography over silica gel (5% methanol in DCM)):

i.r. (CDCl$_3$) 3660, 2960, 2200, 1730, 1625, 1600, 1320, 1140 cm$^{-1}$;

delta$_H$ 8.35 (1H, s), 7.85 (2H, d, J 8.4 Hz), 7.56 (1H, dd, J 6.7, 1.6 Hz), 7.44 (1H, d, J 6.7 Hz), 7.14 (2H, d, J 8.4 Hz), 5.43 (2H, s), 5.17–4.93 (1H, m), 4.04–3.85 (4H, m), 2.57 (3H, s), 1.94–1.76 (2H, m). 1.66–1.51 (1H, m), 1.08–0.77 (12H, m):

delta$_C$ 174.70, 169.59, 156.05, 150.91, 145.03, 140.21, 139.32, 129.83, 129.65, 128.87, 126.81, 111.72, 63.36, 61.46, 61.38, 57.94, 38.95, 24.57, 22.85, 21.22 17.92, 13.64, 13.45.

EXAMPLE 10

N-Methyl-N-4-(5H-2-methylimidazo[4,5-c]pyridylmethyl)phenylsulphonyl-β-alaninc ethyl ester

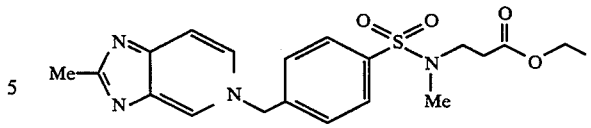

N-Methyl-N-4-(5H-2-methylimidazo[4,5-c]pyridylmethyl)phenylsulphonyl-β-alanine ester was prepared by the procedures of Example 1 Steps (b), (c) and (d) employing β-alanine ethyl ester hydrochloride as starting material and employing 2-methylimidazo[4,5-c]pyridine in lieu of imidazo[4,5-c]pyridine in the final step.

Brown oil (20% yield for last step after chromatography over silica gel (5% methanol in DCM)):

i.r. (CDCl$_3$) 1730, 1630, 1320, 1165 cm$^{-1}$;

delta$_H$ 9.44 (1H, br s), 8.75 (1H, br d, J 6.8 Hz), 8.15 (1H, d, J 6.7 Hz), 7.78 (2H, d, J 8.4 Hz), 7.70 (2H, d, J 8.4 Hz), 6.13 (2H, s), 4.12 (2H, q, J 7.1 Hz), 3.31 (2H, t, J 7.1 Hz), 2.81 (3H, s), 2.77 (3H,s), 2.61 (2H, t, J 7.0 Hz), 1.25 (3H, t, J 7.1 Hz).

EXAMPLE 11

N-Methyl-N-4-(5H-2-methylimidazo[4,5-c]pyridylmethyl)phenylsulphonyl-2-keto-3-amino-4-methylpentane

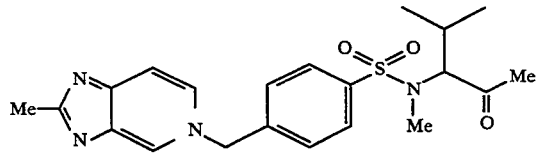

(a) N-Acetyl-2-keto-3-amino-4-methylpentane

A mixture of L-valine (25.0 g, 0.21 mol), acetic anhydride (60.5 ml, 0.64 mol), pyridine (52 ml 0.64 mol) and DMAP (2.0 g, 16.6 mmol) was heated at reflux overnight. The reaction mixture was allowed to cool to room temperature and methanol added with rapid stirring. The mixture was concentrated under reduced pressure to give an oil which was dissolved in diethyl ether (250 ml). washed with 2M hydrochloric acid (150 ml), saturated aqueous sodium hydrogen carbonate (150 ml) and brine (150 ml), dried over anhydrous magnesium sulphate, filtered and evaporated. Distillation under reduced pressure gave N-acetyl-2-keto-3-amino-4-methylpentane (6.3 g, 19%) as a viscous straw coloured oil (76–78° C. @1.5 mmHg).

delta$_H$ 6.92 (1H, br d), 4.41 (1H, dd), 2.09 (1H, m), 2.03 (3H, s), 1.84 (3H, s), 0.80 (3H, d), 0.64 (3H, d).

(b) 2-Keto-3-amino-4-methylpentane hydrochloride

A mixture of N-acetyl-2-keto-3-amino-4-methylpentane (6.33 g, 40.3 mmol) and 6M hydrochloric acid (65 ml) was heated at reflux overnight. The reaction mixture was cooled to room temperature, ethanol (100 ml) was added and the mixture concentrated under reduced pressure. The mixture was triturated with ether to give a precipitate which was collected by filtration. Crystallisation from acetone gave 2-keto-3-amino-4-methylpentane hydrochloride (2.9 g, 63%) as a white crystalline solid.

m.p. 134°–135° C.

delta$_H$ 8.41 (3H, br s), 4.01 (1H, m), 3.72 (br s), 2.34 (1H, m), 2.24 (3H, s), 1.02 (3H, d), 0.87 (3H, s).

(c) N-Methyl-N-4-(5H-2-methylimidazo[4,5-c]pyridylmethyl)phenylsulphonyl-2-keto-3-amino-4-methylpentane N-Methyl-N-4-(5H-2-methylimidazo[4,5-c]pyridyl-methyl)phenylsulphonyl-2-keto-3-amino-4-methylpentane was prepared by the method of Example 1 Step (b) and Step (c) and Example 3 starting from 2-keto-3-amino-4-methylpentane hydrochloride.

Off white solid (12% yield for last step after chromatography over silica get (10% methanol in DCM)):

i.r. (CDCl$_3$) 1715, 1320, 1165 cm$^{-1}$;

delta$_H$ 8.41 (1H, s), 7.78 (2H, d, J 8.4 Hz), 7.63 (2H, br s), 7.26 (2H, d, J 8.3 Hz), 5.54 (2H, s), 4.15 (1H, d, J 10.4 Hz), 2.73 (3H, s), 2.71 (3H, s), 2.16 (3H, s), 2.16–1.99 (1H, m), 0.85 (3H, d, J 6.5 Hz), 0.62 (3H, d, J 6.7 Hz).

EXAMPLE 12

N4-(5H-2-Methylimidazo[4,5-c]pyridylmethyl)-phenylsulphonyl-D-leucinyl allyl ether

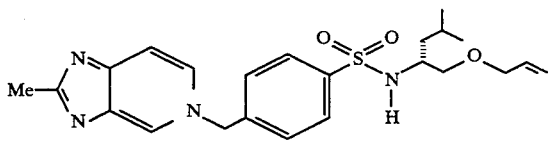

(a) O-allyl-D-leucinyl ether

D-leucinol (30 ml, 235 mmol) was dissolved in dry THF (150 ml) and acetonitrile (20 ml). Sodium Hydride (60% dispersion in oil, 9.39 g, 235 mmol) was added carefully and the resulting mixture was heated to 80° C. for 1 hr. The mixture was allowed to cool, allyl iodide (21.5 ml, 235 mmol) added and the resulting mixture refluxed overnight. On cooling, the products were dissolved in ethyl acetate and washed with brine and water. The organic layer was dried over anhydrous magnesium sulphate filtered and evaporated to dryness under reduced pressure. The oil obtained was purified by distillation under reduced pressure to yield O-allyl-D-leucinyl ether (16.0 g, 44%) as a colourless oil which was used immediately for the next step.

(b) N-4-Bromomethylphenylsulphonyl-D-leucinyl allyl ether

A stirred solution of O-allyl-D-leucinyl ether (16 g, 102 mmol) in dry THF (100 ml) was treated with triethylamine (14.28 ml, 102 mmol) at room temperature. 4-Bromomethylphenylsulphonyl chloride (23 g, 85 mmol) in dry THF (50 ml) was added and the mixture stirred overnight at room temperature. Ethyl acetate was added, the mixture washed with brine, the organic layer separated, dried over anhydrous magnesium sulphate filtered and evaporated under reduced pressure. Purification of the residue by chromatography over silica gel (35% ethyl acetate in hexane) afforded N-4-bromomethylphenylsulphonyl-D-leucinyl allyl ether (16.0 g, 53%) as a white crystalline solid.

delta$_H$ 7.92–7.82 (2H, m), 7.58–7.49 (2H, m), 5.84–5.68 (1H, m), 5.20–5.10 (2H, m), 4.75 (1H, d, J 8.6 Hz), 4.63 (1H, s), 4.50 (1H, s), 3.79 (2H, d, J 5.6 Hz), 3.50–3.39 (1H, m), 3.25 (1H, dd, J 9.4, 3.4 Hz), 3.18, (1H, dd, J 9.5, 4.2 Hz), 1.66–1.22 (3H, m), 0.84 (3H, d, J 6.6 Hz), 0.76 (3H, d, J 6.4 Hz).

(c) N-4-(5H-2-Methylimidazo[4,5-c]pyridylmethyl)-phenylsulphonyl-D-leucinyl allyl ether N-4-(5H-2-Methylimidazo[4,5-c]pyridylmethyl)-phenylsulphonyl-D-leucinyl allyl ether was prepared by the procedure described in Example 1 Step (d) utilising N-4-bromomethylphenylsulphonyl-D-leucinyl allyl ether in lieu of N-methyl-N-4-bromomethylphenylsulphonyl-Leucine ethyl ester and 2-methylimidazo[4,5-c]pyridine in lieu of imidazo[4,5-c]pyridine.

White crystalline solid (18% yield after chromatography over silica (5% methanol in DCM)): m.p. 167° C.

Analysis for C$_{23}$H$_{30}$N$_4$O$_3$S Requires C 62.41 H 6.84 N 12.67 Found C 62.28 H 6.78 N 12.55 i.r. (CDCl$_3$) 2200, 1625, 1315, 1115 cm$^{-1}$;

delta$_H$ 8.47, (1H, s), 7.62 (2H, d, J 8.3 Hz), 7.56 (1H, d, J 6.8 Hz), 7.44 (1H, d, J 6.7 Hz), 7.07 (2H, d, J 8.3 Hz), 5.56–5.35 (3H, m), 4.95–4.52 (2H, m), 3.54 (2H, d, J 5.5 Hz), 3.38–3.25 (1H, m), 3.18–3.02 (2H, m), 2.56 (3H, s), 1.46–1.32, (1H, m), 1.29–1.09 (2H, m), 0.59 (3H, d, J 6.6 Hz), 0.55 (3H, d, J 6.5 Hz).

EXAMPLE 13

N-Methyl-N-4-(5H-2-methylimidazo[4,5-c]pyridyl-methyl)phenylsulphonyl-D-leucinyl allyl ether

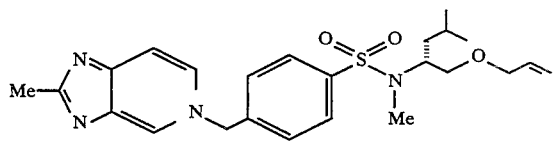

(a) N-Methyl-N-4-bromomethylphenylsulphonyl-D-leucinyl allyl ether

A stirred solution of N-4-bromomethylphenylsulphonyl-D-leucine allyl ether (8.0 g, 22 mmol) in dry THF (150 ml) at 0° C. was treated with sodium hydride (60% dispersion in oil, 0.89 g, 22 mmol) and the mixture stirred until effervescence ceased. Methyl iodide (4.14 ml, 67.5 mmol) was carefully added and the mixture allowed to warm to room temperature with stirring overnight. The mixture was then concentrated by evaporation under reduced pressure, the residue taken up in ethyl acetate and washed with brine. The organic layer was separated, dried over anhydrous magnesium sulphate, filtered and evaporated under reduced pressure to dryness to give crude N-methyl-N-4-bromomethylphenylsulphonyl-D-leucinyl allyl ether which was used directly in the next step.

(b) N-Methyl-N-4-(5H-2-methylimidazo[4,5-c]pyridylmethyl)phenylsulphonyl-D-leucinyl allyl ether N-Methyl-N-4-(5H-2-methylimidazo[4,5-c]pyridyl-methyl)phenylsulphonyl-D-leucinyl allyl ether was prepared by the procedure described in Example 1 Step (d), utilising N-methyl-N-4-bromomethylphenylsulphonyl-D-leucine allyl ether in lieu of N-methyl-N-4-bromomethylphenylsulphonyl-L-leucine ethyl ester and 2-methylimidazo[4,5-c]pyridine in lieu of imidazo[4,5-c]pyridine.

Pale yellow crystalline solid (7% yield after chromatography over silica (6% methanol in DCM)): m.p. 52° C.

i.r. (CDCl$_3$) 2190, 1645, 1570 cm$^{-1}$;

delta$_H$ 8.26 (1H, s), 7.57–7.49 (3H, m), 7.32 (1H, d, J 6.7 Hz), 7.02 (2H, d, J 8.2 Hz), 5.53–5.26 (3H, m), 4.85–4.78 (2H, m), 4.02–3.94 (1H, m), 3.54–3.40 (2H, m), 3.03 (2H, d, J 6.1 Hz), 2.54 (3H, s) 2.46 (3H, s), 1.44–1.28 (1H, m), 1.18–0.92 (2H, m), 0.70 (3H, d, J 6.2 Hz), 0.67 (3H, d, J 6.4 Hz);

delta$_C$ 174.86, 156.24, 145.28, 140.40, 138.48, 133.72, 129.49, 128.53, 127.93, 127.02, 116.56, 111.50, 69.71, 69.37, 61.37, 54.62, 37.40, 27.85, 23.91, 22.69. 21.47, 18.05.

EXAMPLE 14

N-4-(5H-2-Methylimidazo[4,5-c]pyridylmethyl)phenylsulphonyl-L-leucinyl allyl ether

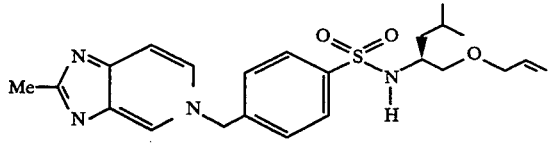

N-4-(5H-2-Methylimidazo[4,5-c]pyridylmethyl)-phenylsulphonyl-L-leucinyl allyl ether was prepared by the procedure described in Example 12 starting from L-leucinol.

White crystalline solid (7% yield for last step after chromatography over silica (5% methanol in DCM)): m.p. 135° C.

Analysis for $C_{23}H_{36}N_4O_3S.0.9H_2O$ Requires C 60.21 H 6.99 N 12.21 Found C 60.07 H 6.77 N 12.36 i.r. (CDCl$_3$) 2200, 1625, 1315, 1115 cm$^{-1}$;

delta$_H$ 8.47. (1H, s), 7.62 (2H, d, J 8.3 Hz), 7.56 (1H, d, J 6.8 Hz), 7.44 (1H 6.7 Hz), 7.07 (2H, d, J 8.3 Hz), 5.56–5.35 (3H, m), 4.95–4.52 (2H, m), 3.54 (2H, d, J 5.5 Hz), 3.38–3.25 (1H, m), 3.18–3.02 (2H, m), 2.56 (3H, s), 1.46–1.32, (1H, m), 1.29–1.09 (2H, m), 0.59 (3H, d, J 6.6 Hz), 0.55 (3H, d, J 6.5 Hz);

EXAMPLE 15

N-Methyl-N-4-(5H-2-methylimidazo[4,5-c]pyridylmethyl)phenylsulphonyl-L-leucinyl allyl ether

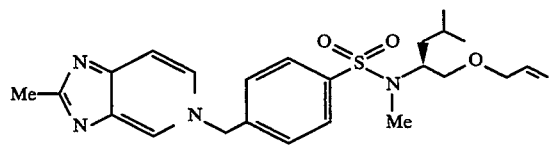

N-Methyl-N-4-(5H-2-methylimidazo[4,5-c]pyridylmethyl)phenylsulphonyl-L-leucinyl allyl ether was prepared by the procedure decribed in Example 13 starting from N-4-bromomethylphenylsulphonyl-L-leucinyl allyl ether.

Colourless oil (8% yield for last step after chromatography over silica (3% methanol in DCM)):

Analysis for $C_{24}H_{32}N_4O_3S.2.0H_2O$

Requires C 58.51 H 7.37 N 11.37 S 6.51 Found C 58.45 H 7.00 N 11.40 S 6.56 i.r. (CDCl$_3$) 2190, 1320, 1145 cm$^{-1}$;

delta$_H$ 8.24 (1H, s), 7.73–7.47 (3H, m), 7.33 (1H, d, J 6.7 Hz), 6.99 (2H, d, J 8.4 Hz), 5.33 (2H, s), 5.39–5.23 (1H, m), 4.90–4.71 (2H, m), 4.00–3.89 (1H, m), 3.51–3.35 (2H, m), 2.99 (2H, d, J 6.2 Hz), 2.50 (3H, s), 2.43 (3H, s), 1.40–1.24 (1H, m), 1.14–0.88 (2H, m), 0.66 (3H, d, J 6.3 Hz), 0.64 (3H, d, J 6.6 Hz).

EXAMPLE 16

N-4-(5H-2-Methylimidazo[4,5-c]pyridylmethyl)phenylsulphonyl-n-propylglycinyl ethyl ether

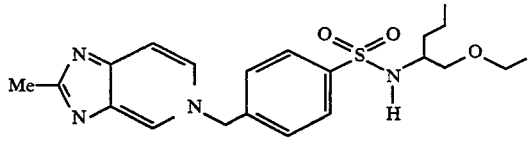

N-4-(5H-2-Methylimidazo[4,5-c]pyridylmethyl)-phenylsulphonyl-n-propylglycinyl ethyl ether was prepared by the procedure of Example 12 starting from D,L-n-propylglycinol.

Colourless amorphous solid (18% yield for last step after chromatography over silica gel (6% methanol in DCM)): m.p. 85° C.

i.r. (CDCl$_3$) 1330, 1155 cm$^{-1}$;

delta$_H$ 8.53 (1H, s), 7.70–7.60 (3H, m), 7.49 (1H, d, J 6.7 Hz), 7.11 (2H, d, J 8.7 Hz), 5.45 (2H, s),3.34–3.20 (1H, m), 3.19–3.00 (4H, m), 2.58 (3H, s), 1.46–1.33 (2H, m), 1.27–0.97 (2H, m), 0.78 (3H, t, J 7.0 Hz), 0.60 (3H, t, J 7.2 Hz);

delta$_C$ 173.73, 155.47, 144.63, 142.64, 140.34, 138.46, 130.25, 129.39, 127.52, 127.37, 111.76, 71.77, 66.01, 61.66, 53.51, 34.17, 18.53, 14.56, 13.42.

EXAMPLE 17

N-Ethyl-N-4-(5H-2-methylimidazo[4,5-c]pyridylmethyl)phenylsulphonyl-n-allylglycinyl ethyl ether

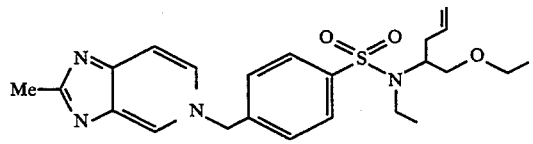

N-Ethyl-N-4-(5H-2-methylimidazo[4,5-c]pyridylmethyl)phenylsulphonyl-n-allylglycinyl ethyl ether was prepared by the method described in Example 1 Steps (b) and (d) starting from N-ethyl-D,L-allylglycinyl ethyl ether and employing 2-methylimidazo[4,5-c]pyridine in lieu of imidazo[4,5-c]pyridine in the final step.

Brown foam (8% yield for last step after chromatography over silica (5% methanol in DCM)):

i.r. (CDCl$_3$) 1625, 1325, 1130 cm$^{-1}$;

delta$_H$ 8.37 (1H, d, J 0.9 Hz), 7.65–7.56 (3H, m), 7.43 (1H, d, J 6.7 Hz), 7.09 (2H, d, J 8.3 Hz), 5.54–5.37 (1H, m), 5.43 (2H, s), 4.90–4.72 (2H, m), 3.87–3.76 (1H, m), 3.22–2.94 (6H, m), 2.57 (3H, s), 2.24–1.96 (2H, m), 1.01 (3H, t J7.0 Hz), 0.76 (3H, t, J 6.9 Hz);

delta$_C$ 174.13, 155.72, 141.79, 138.48, 133.94, 129.97, 128.96, 127.85, 127.26, 117.19, 111.65, 70.34, 65.88, 61.53, 57.58, 38.77, 35.06, 17.83, 16.13.

EXAMPLE 18

N-Ethyl-N-4-(5H-2-methylimidazo[4,5-c]pyridylmethyl)-3-chlorophenylsulphonyl-L-leucinyl ethyl ether

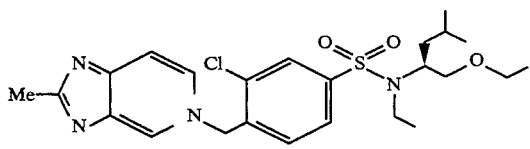

N-Ethyl-N-4-(5H-2-methylimidazo[4,5-c]pyridylmethyl)-3-chlorophenylsulphonyl-L-leucinyl ethyl ether was prepared by the procedure of Example 1 Steps (b) and (d) starting from N-ethyl-L-leucinyl ethyl ether and employing 2methylimidazo[4,5-c]pyridine in lieu of imidazo[4,5-c]pyridine in the final step.

Yellow oil (20% yield for last step after chromatography over silica (5% methanol in DCM)):

i.r. (CDCl₃) 2960, 1625, 1325, 1150 cm⁻¹;

delta$_H$ 8.37 (1H, d, J 1.3 Hz), 7.87 (1H, d, J 1.8 Hz)7.67–7.61 (2H, m), 7.55 (1H, d, J 6.8 Hz), 6.99 (1H, d, J 8.1 Hz), 5.50 (2H, s), 4.02–3.96 (1H, m), 3.21 (2H, d, J 6.4 Hz), 3.19–3.05 (4H, m), 2.68 (3H, s), 1.56–1.51 (1H, m), 1.31–1.15 (2H, m), 1.11 (3H, t, J 7.1 Hz), 0.84 (6H, d, J 5.5 Hz), 0.79 (3H, t, J 7.0 Hz);

delta$_C$ 174.55, 155.94, 144.86, 143.55, 135.77, 133.41, 129.93, 129.21, 129.08. 128.82, 126.30, 111.69, 70.63, 65.90, 59.28, 56.31, 39.72, 38.32, 24.19, 22.54, 21.96, 17.93, 16.22, 14.49.

EXAMPLE 19

N-Isobutoxycarbonyl-N-4-(5H-2-methylimidazo[4,5-c]pyridyimethyl)phenylsulphonyl-L-leucinyl ethyl ether

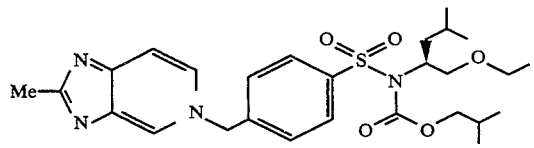

(a) N-Isobutoxycarbonyl-N-4-bromomethylphenylsulphonyl-L-leucinyl ethyl ether

A solution of potassium bis(trimethylsilyl)amide (0.5M in THF, 1 ml, 0.5 mmol) was added to a stirred solution of N-4-bromomethylphenylsulphonyl-L-leucinyl ethyl ether (0.20 g, 0.53 mmol) in dry THF (40 ml) at room temperature under argon. The reaction mixture was cooled to 0° C. and isobutyl chloroformate (0.07 ml, 0.54 mmol) was added. The mixture was allowed to warm to room temperature and was stirred overnight. The solvent was removed under reduced pressure and the residue taken up in ethyl acetate (80 ml) and aqueous ammonium chloride (40 ml) added. The organic layer was separated, washed with brine (40 ml), dried over anhydrous sodium sulphate, filtered and concentrated under reduced pressure. The residue was purified by chromatography (silica: 15% ethyl acetate in hexane) to give N-isobutoxycarbonyl-N-4-bromomethylphenylsulphonyl-L-leucinyl ethyl ether (100 mg, 40%) as a colourless oil.

delta$_H$ 8.07 (2H, m), 7.47 (2H, m), 4.84 (1 H, m), 4.59 (0.8H, s), 4.47 (1.2H, s), 3.95–3.75 (3H, m), 3.60–3.34 (3H, m), 1.98–1.63 (3H, m), 1.41 (1H, m), 1.14 (3H, t, J 7.0 Hz), 1.00 (3H, d, J 6.4 Hz), 0.96 (3H, d, J 6.7 Hz), 0.80–0.74 (6H, m).

(b) N-Isobutoxycarbonyl-N-4-(5H-2-methylimidazo[4,5-c]pyridylmethyl)phenylsulphonyl-L-leucinyl ethyl ether N-Isobutoxycarbonyl-N-4-(5H-2-methylimidazo[4,5-c]pyridylmethyl)phenylsulphonyl-L-leucinyl ethyl ether was prepared by the method of Example 1 Step (d) employing N-isobutoxycarbonyl-N-4-bromomethylphenylsulphonyl-L-leucinyl ethyl ether in lieu of N-methyl-N-4-bromomethylphenylsulphonyl-L-leucine ethyl ester and 2-methylimidazo[4,5-c]pyridine in lieu of imidazo[4,5c]pyridine.

Yellow oil (28% yield after chromatography over silica (4% methanol in chloroform)):

i.r. (CDCl₃) 2200, 1725, 1630, 1320, 1110 cm⁻¹;

delta$_H$8.24 (1H, s), 7.81 (2H, d, J 8.2 Hz), 7.49 (1H, d, J 6.8 Hz), 7.36 (1H, d, J 6.7 Hz), 7.02 (2H, d, J 8.3 Hz), 5.35 (2H, s), 4.65–4.53 (1H, m), 3.68–3.51 (3H, m), 3.41–3.06 (3H, m), 2.52 (3H, s), 1.75–1.39 (3H, m), 1.26–1.11 (1H, m), 0.84–0.72 (9H, m), 0.55 (3H, d, J 6.6 Hz), 0.54 (3H, d, J 6.7 Hz);

delta$_C$ 174.36, 155.86, 151.44, 144.90, 140.46, 139.42, 129.56, 129.06, 128.65, 126.62, 111.39, 72.70, 69.94, 65.68, 61.15, 57.04, 39.09, 26.94, 24.43, 22.53, 21.59, 18.24, 17.77, 14.54.

EXAMPLE 20

N-Ethoxycarbonyl-N-4-(5H-2-methylimidazo[4,5-c]pyridylmethyl)phenylsulphonyl-L-leucinyl ethyl ether

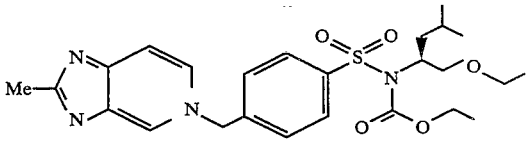

N-Ethoxycarbonyl-N-4-(5H-2-methylimidazo[4,5-c]pyridylmethyl)phenylsulphonyl-L-leucinyl ethyl ether was prepared by the method of Example 19 starting from ethyl chloroformate in lieu of isobutyl chloroformate.

Colourless oil (21% yield for last step):

i.r. (CDCl₃) 2295, 1720, 1625, 1310, 1110 cm⁻¹;

delta$_H$8.22 (1H, s), 7.75 (2H, d, J 8.4 Hz), 7.47 (1H, d, J 8.3 Hz), 7.31 (1H, d, J 6.7 Hz), 6.98 (2H, d, J 8.4 Hz), 5.33 (2H, s), 4.59–4.48 (1H, m), 3.82 (2H, q, J 7.1 Hz), 3.56 (1H, t, J 9.9 Hz), 3.28–3.03 (3H, m), 2.47 (3H, s), 1.66–1.54 (1H, m), 1.47–1.36 (1H, m), 1.18–1.08 (1H, m), 0.84 (3H, t, J 7.2 Hz), 0.79–0.67 (9H, m);

delta$_C$ 174.69, 156.10, 151.18, 145.12, 140.26, 139.45, 129.43, 129.19, 128.46, 126.43, 111.34, 69.95, 65.63, 62.48, 61.09, 56.90, 38.96, 24.38, 22.53, 21.50, 17.87, 14.51, 13.28.

EXAMPLE 21

N-Methyl-N-4-(5H-2-methylimidazo[4,5-c]pyridylmethyl)phenylsulphonyl-L-leucinyl t-butyldiphenylsilyl ether

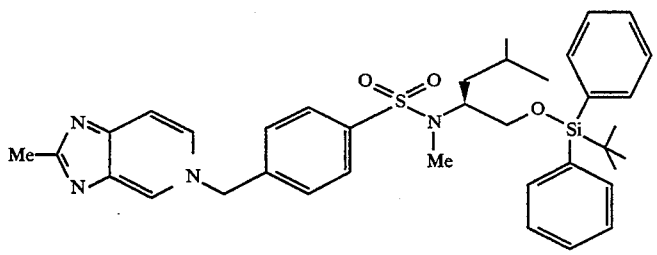

(a) N-4-Bromomethylphenylsulphonyl-L-leucinol

N-4-Bromomethylphenylsulphonyl-L-leucinol was prepared by the method of Example 1 Step (b) employing L-leucinol in lieu of L-leucine ethyl ester hydrochloride and 1.5 equivalents of triethylamine.

Colourless oil: (37% yield after chromatography (silica: 50% ethyl acetate in hexane)).

delta$_H$ 7.91 (2H, d, J 8.3 Hz), 7.53 (2H, d, J 8.4 Hz), 5.31 (1H, d, J 7.7 Hz), 4.62 (2H, s), 3.62–3.44 (2H, m), 3.36–3.27 (1H, m), 2.60 (1H, br s), 1.45–1.37 (1H, m), 1.25 (2H, t, J 7.2 Hz), 0.76 (3H, d, J 6.5 Hz), 0.62 (3H, d, J 6.4 Hz).

(b) N-4-Bromomethylphenylsulphonyl-L-leucinyl t-butyldiphenylsilyl ether t-Butyldiphenylsilyl chloride (12.3 ml. 47.1 mmol) and DMAP (50 mg) were added to a solution of N-4-bromomethylphenylsulphonyl-L-leucinol and diisopropylethylamine (37.3 ml, 0.21 mol) in dry DMF and the mixture stirred at room temperature under argon overnight. Ethyl acetate was added and the mixture washed with aqueous ammonium chloride and brine. The combined aqueous washings were extracted with ethyl acetate and the combined organics dried over anhydrous sodium sulphate filtered and concentrated to give N-4-bromomethyl-phenylsulphonyl-L-leucinyl t-butyldiphenylsilyl ether which was used directly in the next step.

delta$_H$ 8.05–7.31 (14H, m), 4.89 (1H, d, J 10.0 Hz), 4.58 (2H, s), 3.51–3.42 (2H, m), 3.40–3.23 (1H, m), 1.78–1.69 (1H, m), 1.55–1.32 (2H, m), 1.02 (9H, s), 0.77 (3H, d, J 6.6 Hz), 0.72 (3H, d, J 6.5 Hz).

(c) N-Methyl-N-4-(5H-2-methylimidazo[4,5-c]pyridylmethyl)phenylsulphonyl-L-leucinyl t-butyldiphenylsilyl ether N-Methyl-N-4-(5H-2-methylimidazo[4,5-c]pyridylmethyl)phenylsulphonyl-L-leucinyl t-butyldiphenylsilyl ether was prepared by the method of Example 1 Steps (c) and (d) starting from N-4-bromomethylphenylsulphonyl-L-leucinyl t-butyldiphenylsilyl ether and employing and 2-methylimidazo[4,5-c]pyridine in lieu of imidazo[4,5-c]pyridine in the last step.

Off white solid (purified by chromatography over silica gel (10% methanol in DCM)):

i.r. (CDCl$_3$) 3685, 1630, 1600, 1470, 1320 cm$^{-1}$;

delta$_H$ 8.37 (1H, s), 7.65 (2H, d, J 8.3 Hz), 7.58–7.43 (6H, m), 7.40–7.22 (6H, m), 6.99 (2H, d, J 8.3 Hz), 5.41 (2H, s), 4.15–4.02 (1H, m), 3.53 (1H, dd, J 10.7, 5.0 Hz), 3.43 (1H, dd, J 10.7, 6.2 Hz), 2.73 (3H, s), 2.66 (3H, s), 1.43–1.19 (3H, m), 0.97 (9H, br s), 0.80 (6H, t, J 6.2 Hz);

delta$_C$ 174.95, 156.26, 141.04, 138.52, 135.34, 135.28, 132.99, 129.74, 129.67, 128.96, 127.98, 127.56, 127.46, 112.02, 64.50, 61.75, 56.53, 37.43, 28.86, 26.65, 24.25, 22.89, 21.97, 19.03, 18.21.

EXAMPLE 22

N-4-(5H-2-Methylimidazo[4,5-c]pyridylmethyl)phenylsulphonyl-L-leucinyl acetate

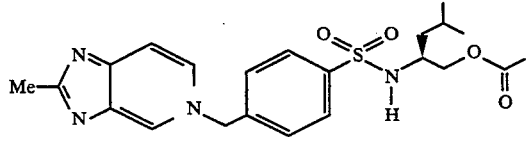

(a) N-4-(5H-2-Methylimidazo[4,5-c]pyridylmethyl)phenylsulphonyl-L-leucinol

N-4-(5H-2-Methylimidazo[4,5-c]pyridylmethyl)phenylsulphonyl-L-leucinol was prepared by the method of Example 1 Steps (b) and (d) starting from L-leucinol in lieu of L-leucine ethyl ester hydrochloride and employing 2-methylimidazo[4,5-c]pyridine in lieu of imidazo[4,5-c]pyridine in the second step.

(b) N-4-(5H-2-Methylimidazo[4,5-c]pyridylmethyl)phenylsulphonyl-L-leucinyl acetate Acetic anhydride (188 μl, 2.0 mmol) was added to a stirred mixture of N-4-(5H$_2$-methylimidazo[4,5-c]pyridylmethyl)phenylsulphonyl-L-leucinol (400 mg, 1.0 mmol), DMAP (20 mg), pyridine (105 μl, 1.3 mmol) in DCM (30 ml) and DMF (10 ml) at 0° C. under argon. The mixture was allowed to warm up to room temperature and stirred overnight. DCM (50 ml) was added and the mixture washed with 1N hydrochloric acid (30 ml), saturated aqueous sodium hydrogen carbonate (50 ml) and brine (50 ml). The organics were dried over anhydrous sodium sulphate filtered and concentrated. Purification of the residue by chromatography over silica gel (30% methanol in DCM) afforded N-4-( 5H-2-methylimidazo[4,5-c]pyridylmethyl)phenylsulphonyl-L-leucinyl acetate (240 mg, 55%) as a colourless oil.

i.r. (CDCl$_3$) 1735, 1355, 1165 cm$^{-1}$;

delta$_H$ 9.32 (1H, s), 8.03 (2H, d, J 8.3 Hz), 7.96–7.88 (2H, m), 7.49 (2H, d, J 8.3 Hz), 5.78 (2H, s), 4.60–4.30 (3H, m), 2.78 (3H, s), 2.25 (3H, s), 1.88–1.54 (3H, m), 0.96 (3H, d, J 6.0 Hz), 0.92 (3H, d, J 6.0 Hz).

EXAMPLE 23

N-Methyl-N-4-(5H-2-methylimidazo[4,5-c]pyridylmethyl)phenylsulphonyl-2-methoxy-3-amino-4-methylpentane

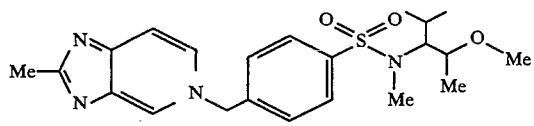

(a) N-Methyl-N-4-bromomethylphenylsulphonyl-2-methoxy-3-amino-4-methylpentane

A stirred solution of N-4-bromomethylphenylsulphonyl-2-hydroxy-3-amino-4-methylpentane (prepared by reduction of the appropriate intermediate from the synthesis of Example 11 with sodium borohydride) (1.45 g, 4.14 mmol) in DCM (50 ml) was treated with sodium hydride (60% dispersion in oil: 166 m, 4.15 mmol) at 0° C. The reaction mixture was stirred for 0.5 h and methyl iodide (1 ml, 16 mmol) added and the mixture allowed to warm to room temperature. Aqueous ammonium chloride was added and the organic layer separated, dried over arthydrous sodium sulphate, filtered and evaporated to give crude N-methyl-N-4-bromomethylphenylsulphonyl-2-methoxy-3-amino-4-methylpentane as an oil, which was used in the next step without further purification.

(b) N-Methyl-N-4-(5H-2-methylimidazo[4,5-c]pyridylmethyl)phenylsulphonyl-2-methoxy-3-amino-4-methylpentane N-Methyl-N-4-(5H-2-methylimidazo[4,5-c]pyridylmethyl)phenylsulphonyl-2-methoxy-3-amino-4-methylpentane was prepared by the procedure of Example 1 Step (d) employing N-methyl-N-4-bromomethylphenylsulphonyl-2-methoxy-3-amino-4-methylpentane in lieu of N-methyl-N-4-bromomethylphenylsulphonyl-L-leucine ethyl ester and 2-methylimidazo[4,5-c]pyridine in lieu of imidazo[4,5-c]pyridine.

Colourless oil (3% yield for last step after chromatography over silica gel (5% methanol in DCM)):

i.r. (CDCl$_3$) 1380, 1150 cm$^{-1}$;

delta$_H$ 8.49 (1H, br s), 7.76 (2H, d, J 8.3 Hz), 7.73–7.58 (2H, m), 7.20 (2H, d J 8.3 Hz), 5.52 (2H, s), 3.98–3.88 (1H, m), 3.58 (1H, dd, J 9.2, 4.5 Hz), 3.45 (3H, s), 2.73 (3H, s), 2.69 (3H, s), 1.98–1.83 (1H, m), 1.08 (3H, d, J 6.6 Hz), 0.93 (3H, d, J 6.6 Hz), 0.67 (3H, d, J 6.7 Hz);

delta$_C$ 174.69, 156.07, 144.99, 140.92, 140.67, 138.79, 137.63, 130.24, 129.21, 128.37, 127.64, 112.12, 67.98, 66.83, 61.87, 50.12, 30.38, 26.94, 21.79, 20.91, 19.95.

EXAMPLE 24

Inhibition of [$^3$H]-PAF Receptor Binding

The inhibition of [$^3$H]-PAF binding to human platelet plasma membrane by compounds of general formula I is determined by isotopic labelling and filtration techniques. Platelet concentrates are obtained from a hospital blood bank. These platelet concentrates (500–2500 ml.) are centrifuged at 800 rpm for 10 minutes in a SORVALL RC3B centrifuge to remove the red blood cells present. (The word SORVALL is a trade mark.) The supernatant is subsequently centrifuged at 3,000 rpm in a SORVALL RC3B centrifuge to pellet the platelets present. The platelet rich pellets are resuspended in a minimum volume of buffer (150 mM NaCl, 10 mM Tris, 2 mM EDTA, pH 7.5) and layered onto Ficoll-Paque gradients, 9 ml platelet concentrate to 2 ml Ficoll, and centrifuged at 1,900 rpm for 15 minutes in a SORVALL RT6000 centrifuge. This step removes the residual red blood cells and other nonspecific material such as lymphocytes from the preparation. The platelets which form a band between the plasma and the Ficoll are removed, resuspended in the above buffer and centrifuged at 3,000 rpm for 10 minutes in a SORVALL RT6000 centrifuge. The pelleted platelets are resuspended in buffer (10 mM Tris, 5 mM MgCl$_2$, 2 mM EDTA, pH 7.0), snap freezed in liquid N$_2$ and allowed to thaw slowly at room temperature in order to lyse the platelets. The latter step is repeated at least 3 times to ensure proper lysis. The lysed platelets are centrifuged at 3,000 rpm for 10 minutes in a SORVALL RT6000 centrifuge and resuspended in buffer. The latter step is repeated twice in order to remove any cytoplasmic proteins which may hydrolyse the platelet activating factor (PAF) receptor. The prepared platelet membranes may be stored at $-70°$ C. After thawing the prepared membranes are centrifuged in a SORVALL RT6000 at 3,000 rpm for 10 minutes and resuspended in assay buffer.

The assay is conducted by preparing a series of Tris-buffered solutions of the selected antagonist of predetermined concentrations. Each of these solutions contained [$^3$H]-PAF (0.5 nM; 1-O-[$^3$H]octadecyl-2-acetyl-sn-glycero-3-phosphoryl choline with a specific activity of 132 Ci/mmol), unlabelled PAF (1000 nM), a known amount of the test antagonist, and a sufficient amount of Tris-buffer solution (10 mM Tris, 5 mM MgC$_2$, pH 7.0, 0.25% BSA) to make the final volume 1 ml. Incubation is initiated by the addition of 100 $\mu$g of the isolated membrane fraction to each of the above solutions at 0° C. Two control samples, one (C1) which contained all the ingredients described above except the antagonist and the other (C2) contains C1 plus a 1000-fold excess of unlabelled PAF, are also prepared and incubated simultaneously with the test samples. After 1 hour incubation, each solution is filtered rapidly under vacuo through a WHATMAN GF/C glass fibre filter in order to separate unbound PAF from bound PAF. (The word WHATMAN is a trade mark.) The residue in each case is rapidly washed 4 times with 5 ml cold (4° C.) Tris-buffer solution. Each washed residue is dried under vacuum on a sampling manifold and placed into vials containing 20 ml of OPTIPHASE MP scintillation fluid and the radioactivity counted in a liquid scintillation counter. (The word OPTIPHASE is a trade mark.) Defining the counts for total binding with antagonist from a test sample as "TBA"; the counts for total binding from the control sample C1 as "TB"; and the counts for nonspecific binding from the control sample C2 as "NSB"; the percent inhibition of each test antagonist can be determined by the following equation:

$$\%\text{Inhibition} = [(TB-TBA)/SB] \times 100$$

where the specific binding SB=TB-NSB

Table 1 lists results from this assay for inhibition of [$^3$H]-PAF receptor binding for illustrative examples of the compounds of this invention.

TABLE 1

| Results for inhibition of [$^3$H]-PAF receptor binding | |
|---|---|
| Example | Inhibition of [$^3$H]-PAF binding IC$_{50}$ nM |
| 1 | 5 |
| 4 | 10 |
| 5 | 2 |

TABLE 1-continued

| Results for inhibition of [³H]-PAF receptor binding | |
|---|---|
| Example | Inhibition of [³H]-PAF binding IC$_{50}$ nM |
| 6 | 10 |
| 8 | 15 |
| 21 | 20 |
| 23 | 15 |

We claim:

1. A compound of formula I;

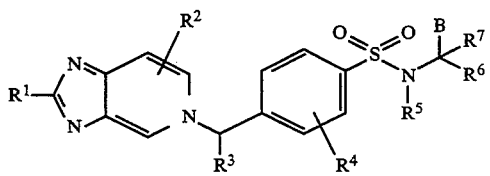

wherein:
each of $R^1$ and $R^3$ independently represents hydrogen or a —$C_1$-$C_6$ alkyl group;
$R^2$ represents a group substituted at one or more of the 4, 6 or 7 positions of the imidazo[4,5-c]pyridine heterocycle, said group(s) being independently selected from hydrogen, —$C_1$-$C_6$ alkyl, —$OC_1$-$C_6$ alkyl, or halogen;
$R^4$ represents hydrogen, —$C_1$-$C_6$ alkyl, —$OC_1$-$C_6$ alkyl, or a halogen;
$R_5$ represents hydrogen, —$C_1$-$C_6$ alkyl, —$C_2$-$C_6$ alkenyl, —$C_2$-$C_6$ alkynyl, —$COC_1$-$C_6$ alkyl, —$CO_2C_1$-$C_6$ alkyl, —$(COC_1$-$C_6$ alkyl)phenyl, —$(CO_2C_1$-$C_6$ alkyl)phenyl, —$(C_1$-$C_6$ alkyl)$OC_1$-$C_6$ alkyl, —$(C_1$-$C_6$ alkyl)$SC_1$-$C_6$ alkyl, —$(C_1$-$C_6$ alkyl)$CO_2C_1$-$C_6$ alkyl, —$C_3$-$C_8$ cycloalkyl, —$C_4$-$C_8$ cycloalkenyl or a group —D
wherein D represents a group;

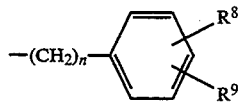

wherein n is an integer from 0 to 3, and each of $R^8$ and $R^9$ is independently hydrogen, —$C_1$-$C_6$ alkyl, —$C_2$-$C_6$ alkenyl, —$C_2$-$C_6$ alkynyl, halogen, —CN, —$CO_2$H, —$CO_2C_1$-$C_6$ alkyl, —$CONH_2$, —$CONHC_1$-$C_6$ alkyl, —$CON(C_1C_6$ alkyl)$_2$, —CHO, —$CH_2OH$, —$CF_3$, —$OC_1$-$C_6$ alkyl, —$SC_1$-$C_6$ alkyl, —$SOC_1$-$C_6$ alkyl, —$SO_2C_1$-$C_6$ alkyl, —$NH_2$ or —NHCOMe;
each of $R^6$ and $R^7$ independently represent hydrogen, halogen, —$C_1$-$C_6$ alkyl optionally substituted by one or more halogen atoms, —$C_2$-$C_6$ alkenyl, —$C_2$-$C_6$ alkynyl, —$(C_1$-$C_6$ alkyl)$CO_2C_1$-$C_6$ alkyl, —$(C_1$-$C_6$ alkyl)$SC_1$-$C_6$ alkyl, —$(C_1$-$C_6$ alkyl)$OC_1$-$C_6$ alkyl, —$(C_1$-$C_6$ alkyl)$N(C_1$-$C_6$ alkyl)$_2$, —$C_3$-$C_8$ cycloalkyl, —$C_4$-$C_8$ cycloalkenyl, —$(C_1$-$C_6$ alkyl)$C_3$-$C_8$ cycloalkyl, —$(C_1$-$C_6$ alkyl)$C_4$-$C_8$ cycloalkenyl, —$(C_1$-$C_6$ alkyl)$OC_3$-$C_8$ cycloalkyl, —$(C_1$-$C_6$ alkyl)$OC_4$-$C_8$ cycloalkenyl, —$(C_1$-$C_6$ alkyl)$SC_3$-$C_8$ cycloalkyl, —$(C_1$-$C_6$ alkyl)$SC_4$-$C_8$ cycloalkenyl, a side chain of a naturally occurring amino acid, a group -D, or a —$(C_1$-$C_6$ alkyl)OD group wherein D is as defined above;
or $R^5$ together with $R^6$ or $R^7$ and the atoms to which they are attached form a 5 to 8 membered nitrogen-containing heterocyclic ring;
or $R^6$ and $R^7$ together with the carbon atom to which they are attached form a $C_3$-$C_8$ cycloalkyl ring;
B represents a) a -$(CH_2)_m$A group wherein m is an integer from 0 to 1 and the group A represents a 5- or 6-membered heterocyclic ring, which heterocyclic ring may be optionally fused to a benzene ring or to a further 5-, 6- or 7-membered, heterocyclic ring containing one or more nitrogen atoms, wherein at least one, of the said heterocyclic tings may also contain an oxygen or sulphur atom, and wherein any of the rings may be optionally substituted with one or more substituents selected from hydrogen, halogen, —$C_1$-$C_4$ perfluoroalkyl, hydroxyl, carboxyl, —$CONH_2$, a group —D wherein D is as defined above, —$R^{10}$, —$OR^{10}$, —$SR^{10}$, —$SOR^{10}$, $SO_2R^{10}$, —$NHR^{10}$, —$NR^{10}R^{10}$, —$CO_2R^{10}$ or —$CONHR^{10}$ wherein $R^{10}$ is —$C_1$-$C_6$ alkyl, —$C_2$-$C_6$ alkenyl, —$C_2$-$C_6$ alkynyl, —$C_3$-$C_8$ cycloalkyl or —$C_4$-$C_8$ cycloalkenyl each of which is optionally substituted with one or more substituents selected from halogen, hydroxyl, amino, carboxyl, —$C_1$-$C_4$ perfluoroalkyl, —$C_1$-$C_6$ alkyl, —$C_2$-$C_6$ alkenyl, —$C_2$-$C_6$ alkynyl, —$C_3$-$C_8$ cycloalkyl, —$C_4$-$C_8$ cycloalkenyl, —$OC_1$-$C_6$ alkyl, —$SC_1$-$C_6$ alkyl, tetrazol-5-yl, a group —D wherein D is as defined above or a heteroaryl or heteroarylmethyl group;
b) a —$ZR^{11}$ group wherein Z is —C(=O)—, —C(=O)O—, —C(=O)S—, —($C_1$-$C_6$ alkyl)O—, —($C_1$-$C_6$ alkyl)OC(=O)—, —C(=S)—, —C(=S)O—, —($C_1$-$C_6$ alkyl)S—, —($C_1$-$C_6$ alkyl)OC(=O)C(=O)O—, —($C_1$-$C_6$ alkyl)OSO$_2$—, —NHC(=O)O—, —($C_1$-$C_6$ alkyl)OC(=O)NH—, —($C_1$-$C_6$ alkyl)C(=O)O— group, or —($C_1$-$C_6$ alkyl)OSi($C_1$-$C_6$ alkyl)$_2$—, —($C_1$-$C_6$ alkyl)OSiPh$_2$- group and $R^{11}$ is hydrogen, —$C_1$-$C_{18}$ alkyl, —$C_2$-$C_{18}$ alkenyl, —$C_2$-$C_{18}$ alkynyl, —($C_1$-$C_6$ alkyl)$OC_1$-$C_6$ alkyl, —($C_1$-$C_6$ alkyl)$SC_1$-$C_6$ alkyl, —($C_1$-$C_6$ alkyl)$O(C_1$-$C_6$ alkyl)$OC_1$-$C_6$ alkyl, —$C_3$-$C_8$ cycloalkyl, —$C_4$-$C_8$ cycloalkenyl, a group D as defined above or a group A as defined above;
c) a —$CH_2NR^{12}R^{13}$ group or a —$CONR^{12}R^{13}$ group wherein each of $R^{12}$ and $R^{13}$ is independently hydrogen, —$C_1$-$C_6$ alkyl, —$C_3$-$C_8$ cycloalkyl, pyridyl, a group D as defined above or $R^{12}$ and $R^{13}$ together with the nitrogen atom to which they are attached form a 5 to 8 membered nitrogen-containing heterocyclic ring;
or a pharmaceutically or veterinarily acceptable acid addition salt or hydrate thereof.

2. A compound as claimed in claim 1, in which $R^1$ represents a hydrogen atom or a $C_1$-$C_6$ alkyl group.

3. A compound as claimed in claim 1, wherein $R^2$ represents a hydrogen atom.

4. A compound as claimed in claim 1, wherein $R^3$ represents a hydrogen atom.

5. A compound as claimed in claim 1, wherein $R^4$ represents a hydrogen atom or a halogen atom.

6. A compound as claimed in claim 1, wherein $R^5$ represents a hydrogen atom, a —$C_1$-$C_6$ alkyl group, a —$CO_2C_1$-$C_6$ alkyl group, or a —($C_1$-$C_6$ alkyl)$CO_2C_1$-$C_6$ alkyl group.

7. A compound as claimed in claim 1, wherein $R^6$ represents a hydrogen atom.

8. A compound as claimed in claim 1, wherein $R^7$ represents a hydrogen atom, a —$C_1$-$C_6$ alkyl group, a —$C_1$-$C_6$ alkenyl group, or the side chain of a naturally occurring amino acid, wherein the stereochemistry of the carbon atom to which R⁶ and R⁷ are attached is the same as, or the opposite to, that of the naturally occurring amino acid.

9. A compound as claimed in claim 1, wherein B represents a ZR¹¹ group, wherein
Z represents a —C(=O)— group, —C(=O)O— group, a —(C₁-C₆ alkyl)OC(=O)— group, a —(C₁-C₆ alkyl)O— group, a —(C₁-C₆ alkyl)C(=O)O— group, or a —(C₁-C₆ alkyl)OSiPh₂— group.

10. A compound as claimed in claim 1, wherein R¹¹ represents a —C₁-C₁₈ alkyl group, a —C₂-C₁₈ alkenyl group or a group D.

11. A compound as claimed in claim 1, wherein n represents an integer of 1.

12. A compound as claimed in claim 1, wherein R⁸ represents a hydrogen atom.

13. A compound as claimed in claim 1, wherein R⁹ represents a hydrogen atom.

14. A compound according to claim 1 which is:
N-Methyl-N-4-(5H-imidazo[4,5-c]pyridylmethyl)-phenylsulphonyl-L-leucine ethyl ester,
N-Methyl-N-4-(5H-2-methylimidazo[4,5-c]pyridylmethyl)phenylsulphonyl-L-leucine ethyl ester,
N-Methyl-N-4-(5H-2-methylimidazo[4,5-c]pyridylmethyl)phenylsulphonyl-L-leucine benzyl ester.
N-Methyl-N-4-(5H-2-methylimidazo[4,5-c]pyridylmethyl)phenylsulphonyl-L-isoleucine allyl ester,
N-Methyl-N-4-(5H-2-methylimidazo[4,5-c]pyridylmethyl)-3-chloro-phenylsulphonyl-L-leucine ethyl ester.
N-Ethoxycarbonylmethyl-N-4-(5H-2-methylimidazo[4,5-c]pyridylmethyl)phenylsulphonyl-L-leucine ethyl ester.
N-Methoxycarbonylmethyl-N-4-(5H-2-methylimidazo[4,5-c]pyridylmethyl)phenylsuiphonyl-L-leucine ethyl ester,
N-t-Butyloxycarbonylmethyl-N-4-(5H-2-methylimidazo[4,5-c]pyridyl-methyl)phenylsulphonyl-L-leucine ethyl ester.
N-Ethoxycarbonyl-N-4-(5H-2-methylimidazo[4,5-c]pyridylmethyl)phenyl-suiphonyl-L-leucine ethyl ester,
N-Methyl-N-4-(5 H-2-methylimidazo[4,5 -c]pyridylmethyl)phenysulphonyl-β-alanine ethyl ester.
N-Methyl-N-4-(5H-2-methylimidazo[4,5-c]pyridylmethyl)phenylsulphonyl- 2-keto-3-amino-4-methylpentane,
N-4-(5H-2-Methylimidazo[4,5-c]pyridylmethyl)phenylsulphonyl-D-leucinyl allyl ether,
N-Methyl-N-4-(5H-2-methylimidazo[4,5-c]pyridylmethyl)phenylsulphonyl-D-leucinyl allyl ether,
N-4-(5H-2-Methylimidazo[4,5-c]pyridylmethyl)phenylsulphonyl-L-leucinyl allyl ether,
N-Methyl-N-4-(5H-2-methylimidazo[4,5-c]pyridylmethyl)phenylsulphonyl-L-leucinyl allyl ether,
N-N-4-(5H-2-Methylimidazo[4,5-c]pyridylmethyl)-phenylsulphonyl-n-propylglycinyl ethyl ether,
N-Ethyl-N-4-(5H-2-methylimidazo[4,5-c]pyridylmethyl)phenylsulphonyl-n-allylglycinyl ethyl ether,
N-Ethyl-N-4-(5H-2-methylimidazo[4,5-c]pyridylmethyl)-3-chlorophenyl-sulphonyl-L-leucinyl ethyl ether,
N-Isobutoxycarbonyl-N -4-(5 H-2-methylimidazo[4,5-c]pyridylmethyl)phenyl-sulphonyl-L-leucinyl ethyl ether,
N-Ethoxycarbonyl-N-4-(5H-2-methylimidazo[4,5-c]pyridylmethyl)phenyl-sulphonyl-L-leucinyl ethyl ether,
N-Methyl-N-4-(5H-2-methylimidazo[4,5-c]pyridylmethyl)phenylsulphonyl-L-leucinyl t-butyldiphenylsilyl ether,
N-4-(5H-2-Methylimidazo[4,5-c]pyridylmethyl)phenyl-sulphonyl-L-leucinyl acetate.
N-Methyl-N-4-(5H-2-methylimidazo[4,5-c]pyridylmethyl)phenylsulphonyl-2-methoxy-3-amino-4-methylpentane,
or a pharmaceutically acceptable salt of such a compound.

15. A pharmaceutical or veterinary composition comprising a compound as claimed in claim 1 and a pharmaceutically and/or veterinarily acceptable carrier.

16. A method for the treatment or prophylaxis of diseases or conditions mediated by platelet activating factor, the method comprising administering to a patient an effective amount of a compound as claimed in claim 1.

* * * * *